US006555657B2

(12) United States Patent
Christensen

(10) Patent No.: US 6,555,657 B2
(45) Date of Patent: Apr. 29, 2003

(54) ISOLATED TRANSCRIPTION FACTOR FOR AN ALPHA-AMYLASE PROMOTER IN FILAMENTOUS FUNGI

(75) Inventor: Tove Christensen, Lyngby (DK)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 09/920,581

(22) Filed: Aug. 1, 2001

(65) Prior Publication Data

US 2002/0151073 A1 Oct. 17, 2002

Related U.S. Application Data

(62) Division of application No. 09/197,814, filed on Nov. 23, 1998, now Pat. No. 6,316,220, which is a continuation of application No. PCT/DK00/00305, filed on Jul. 7, 1997.

(30) Foreign Application Priority Data

Jul. 5, 1996 (DK) .................................. 0740/96

(51) Int. Cl.7 ..................... C07K 14/37; C07K 14/375; C07K 14/38
(52) U.S. Cl. ........................................ 530/350
(58) Field of Search ......................... 530/350

(56) References Cited

PUBLICATIONS

Verdoes, Jan C et al., Gene, vol. 145(2), pp. 179–187, (1994).
Verdoes, Jan C et al., Appl. Microbiol Biotechnology vol. 43: pp. 195–205, (1995).
Nagata, O et al., Mol. Gen. Genet (Germany) vol. 237 (1–2) pp. 251–260, (1993).
Dhawale, S.et al., Nucleic Acids Research, vol. 21, No. 24, pp. 5537–5546 (1993).
Tada, Setsuzu et al., Mol. Gen Genet, vol. 229: pp. 301–306, (1991).
Lachmund, Astrid et al., Current Microbiology vol. 26, pp. 47–51,(1993).
Kelly, Rosemary et al., Journal of Bacteriology, vol. 174, No. 1, pp. 222–232,(1992).

*Primary Examiner*—Terry McKelvey
(74) *Attorney, Agent, or Firm*—Elias J. Lambiris

(57) ABSTRACT

The present invention relates to a transcription factor found in filamentous fungi, especially in Aspergillii, DNA sequences coding for said factor, its transformation into and expression in fungal host organisms, and the use of said factor in such hosts for increasing the expression of a polypeptide of interest being produced by said host.

13 Claims, 8 Drawing Sheets

ISOLATED TRANSCRIPTION FACTOR FOR AN ALPHA-AMYLASE PROMOTER IN FILAMENTOUS FUNGI

CROSS-REFERENCE TO RELATED APPLICATIONS

This application is a divisional of U.S. application Ser. No. 09/197,814 filed Nov. 23, 1998, now U.S. Pat. No. 6,316,220, which is a continuation of PCT/DK97/00305 filed Jul. 7, 1997 (the international application was published under PCT Article 21(2) in English) and claims, under 35 U.S.C. 119, priority of Danish application no. 0740/96 filed Jul. 5, 1996, the contents of which are fully incorporated herein by reference.

FIELD OF THE INVENTION

The present invention relates to a transcription factor found in filamentous fungi, especially in Aspergillii, DNA sequences coding for said factor, its transformation into and expression in fungal host organisms, and the use of said factor in such hosts for increasing the expression of a polypeptide of interest being produced by said host.

BACKGROUND OF THE INVENTION

Transcription factors are well known proteins involved in the initiation of transcription. They have been studied intensively in many different organisms and have also been described in fungi. Dhawale and Lane (NAR (1993) 21 5537–5546) have recently compiled the transcription factors from fungi, including the filamentous fungi.

Many of the transcription factors are regulatory proteins; they bind to the promoter DNA and either activate or repress transcription as a response to stimuli to the cell.

The expression of the α-amylase gene in *A. oryzae* is regulated in response to the available carbon source. The gene is expressed at its maximum when the organism is grown on starch or maltose (Lachmund et al. (1993) *Current Microbiology* 26 47–51; Tada et al. (1991) *Mol. Gen. Genet* 229 301–306). The expression of α-amylase is regulated at the transcriptional level as shown by Lachmund et aL (supra), which strongly suggests that transcription factors are involved in the regulation, but so far no gene for such a factor has been identified.

The promoter of the α-amylase gene has been studied by deletion analysis (Tada et al. (1991) *Agric. Biol. Chem.* 55 1939–1941; Tsuchiya et al. (1992) *Biosci. Biotech. Biochem.* 56 1849–1853; Nagata et al. (1993) *Mol. Gen. Genet* 237 251–260). The authors of these papers propose that a specific sequence of the promoter is responsible for the maltose induction. Nagata et al. (supra) used this sequence as a probe in a gel shift experiment to see whether any proteins from *A. nidulans* nuclear extracts were able to bind to the promoter sequence. Three such proteins were found, but no involvement of these proteins in expression was shown. None of the proteins have been purified or identified by other means. Their genes likewise remain unknown.

SUMMARY OF THE INVENTION

The present invention relates to a transcription factor regulating the expression of the α-amylase promoter in filamentous fungi.

Accordingly, in a first aspect the invention relates to a DNA construct comprising a DNA sequence encoding a transcription factor of the invention, which DNA sequence comprises:

a) the transcription factor encoding part of the DNA sequence cloned into plasmid pToC320 present in *E. coli* ToC1058, DSM 10666, or b) an analogue of the DNA sequence defined in a), which
  i) is at least 60% homologous with the DNA sequence defined in a), or
  ii) hybridizes with the same nucleotide probe as the DNA sequence defined in a), or
  iii) encodes a transcription factor which is at least 50% homologous with the transcription factor encoded by a DNA sequence comprising the DNA sequence defined in a), or
  iv) encodes a transcription factor which is immunologically reactive with an antibody raised against the purified transcription factor encoded by the DNA sequence defined in a), or
  v) complements the mutation in ToC879, i.e. enables ToC879 to grow on cyclodextrin and produce lipase when transformed with said DNA sequence.

The full length genomic DNA sequence encoding a transcription factor has been derived from a strain of the filamentous fungus *Aspergillus oryzae* and has been cloned into plasmid pToC320 present in *E. coli* ToC1058, DSM 10666.

Said transcription factor encoding DNA sequence harboured in pToC320, DSM 10666, is believed to have the same sequence as that presented in SEQ ID NO: 1 and SEQ ID NO: 2. Accordingly, whenever reference is made to the transcription factor encoding part of the DNA sequence cloned into plasmid pToC320 present in DSM 10666 such reference is also intended to include the transcription factor encoding part of the DNA sequence presented in SEQ ID NO: 1 and SEQ ID NO: 2.

Accordingly, the terms "the transcription factor encoding part of the DNA sequence cloned into plasmid pToC320 present in DSM 10666" and "the transcription factor encoding part of the DNA sequence presented in SEQ ID NO: 1 and SEQ ID NO: 2" may be used interchangeably.

In further aspects the invention provides an expression vector harbouring the DNA construct of the invention, a cell comprising said DNA construct or said expression vector and a method of producing a peptide exhibiting transcription factor activity, which method comprises culturing said cell under conditions permitting the production of the transcription factor.

Such a transcription factor of the invention will typically originate from a filamentous fungus.

The term "filamentous fungus" is intended to include the groups Phycomycetes, Zygomycetes, Ascomycetes, Basidiomycetes and fungi imperfecti, including Hyphomycetes such as the genera Aspergillus, Penicillium, Trichoderma, Fusarium and Humicola.

The invention also relates to a method of producing a filamentous fungal host cell comprising the introduction of a DNA fragment coding for any such factor into a filamentous fungus wherein an α-amylase promoter or a co-regulated promoter regulates the expression of a polypeptide of interest in a manner whereby said factor will be expressed in said fungus.

In a further aspect the invention relates to a method of producing a polypeptide of interest, the expression of which is regulated by an α-amylase promoter or a co-regulated promoter, comprising growing a filamentous fungal host cell as described above under conditions conducive to the production of said factor and said polypeptide of interest, and recovering said polypeptide of interest.

Finally the invention relates to the use of said factor for regulating the expression of a polypeptide of interest in a filamentous fungus.

In this context, regulation means to change the conditions under which the factor of the invention is active. This could mean different pH, substrate, etc. regimes, whereby the resulting effect is an improved regulation of the expression of the protein of interest.

Furthermore, regulation also comprises events occurring in the growth phase of the fungus during which the transcription factor is active. Depending on the circumstances, both advancing and/or postponing the phase wherein the factor is active may enhance the expression and thus the yield.

In addition, using standard procedures known in the art, the specific DNA sequences involved in the binding of a transcription factor may be identified, thereby making it possible to insert such sequences into other promoters not normally regulated by the factor and enabling those promoters to be under the regulation of said factor.

BRIEF DESCRIPTION OF THE TABLES AND DRAWING

Figure 7:
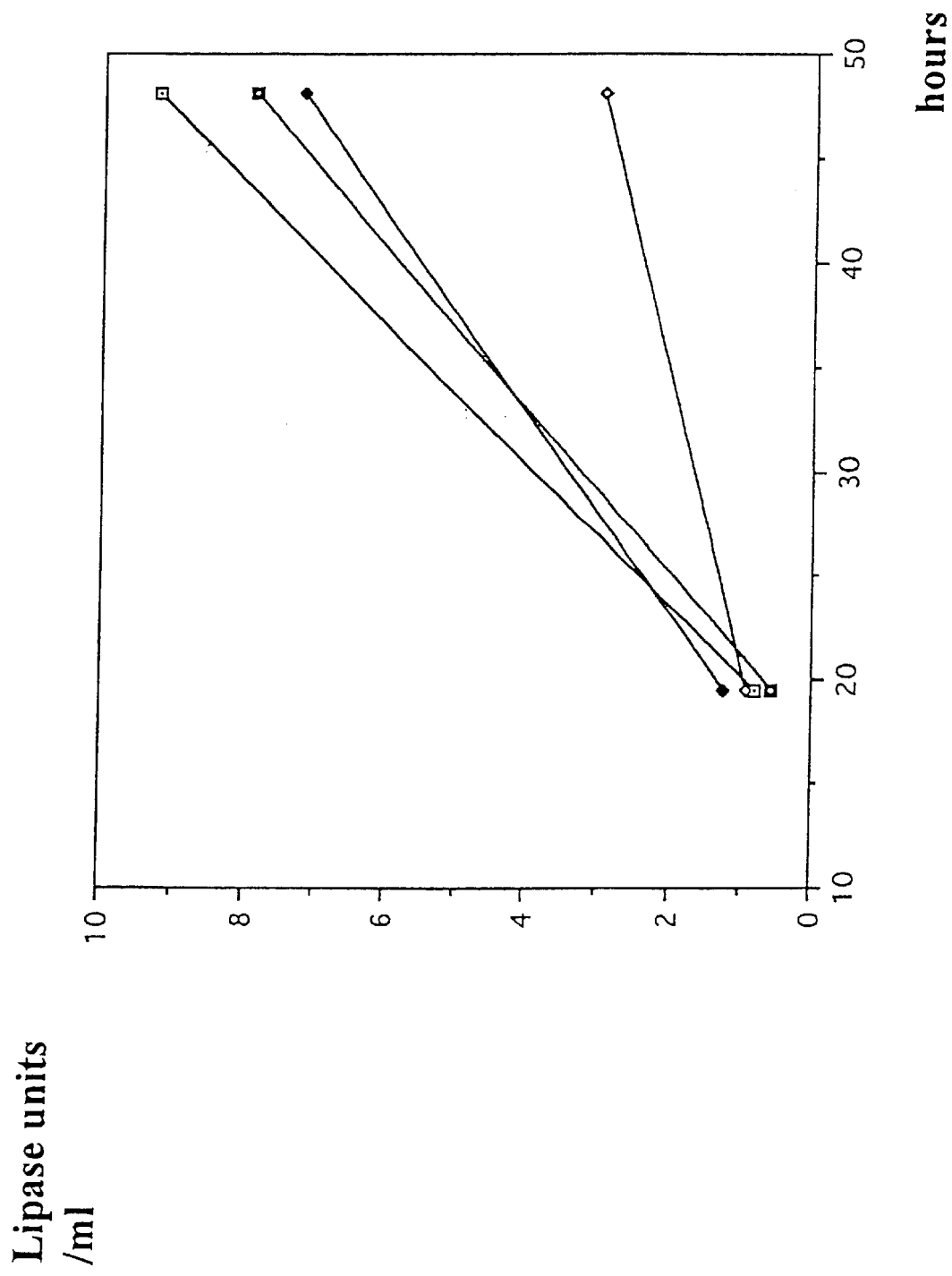
Figure 8:
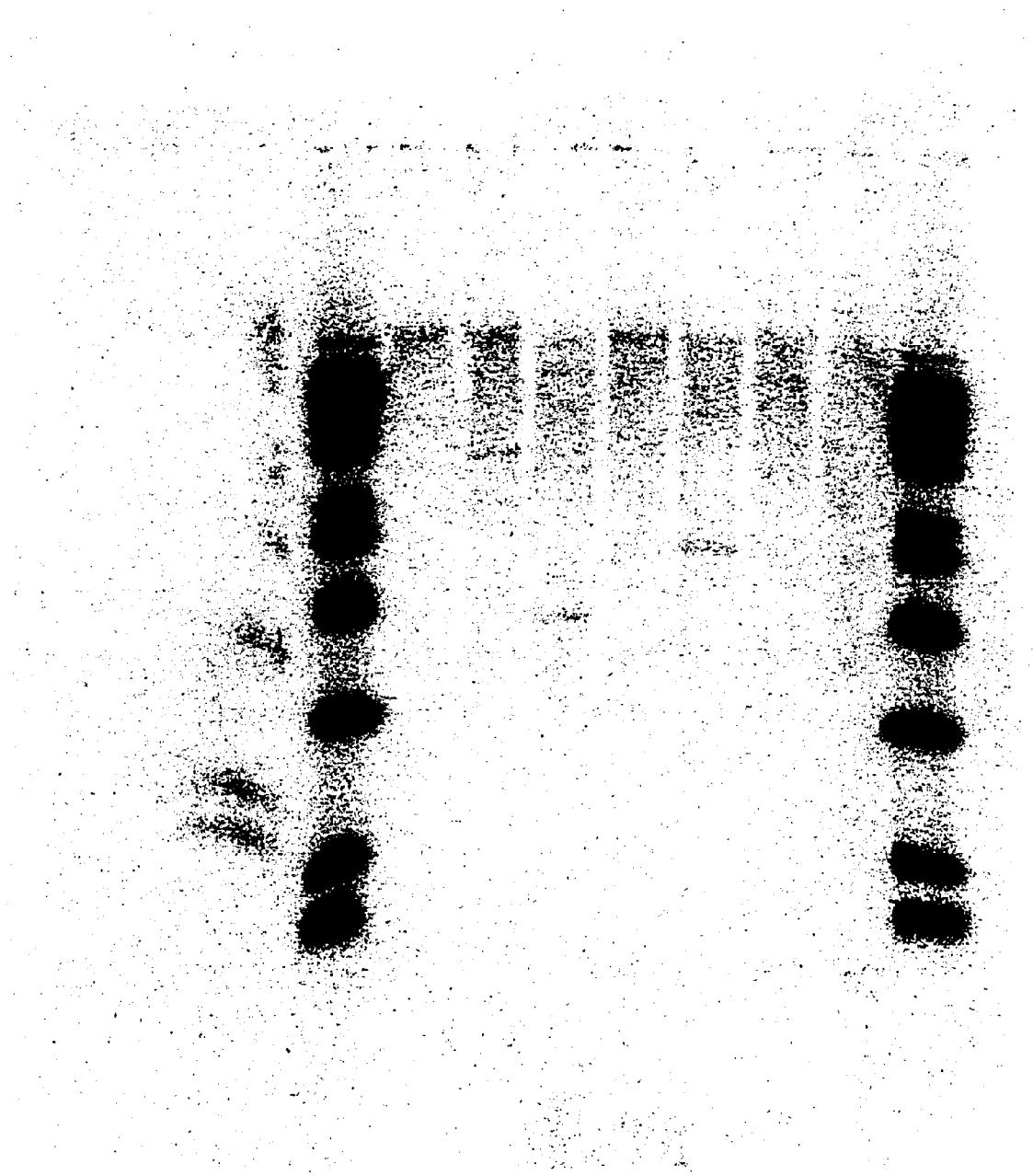

FIG. 7 shows the results of lipase production by ToC1139 cultured in YP media containing 2% glucose (-|-) or 10% glucose (-?-), in comparison to ToC1075 cultured in YP media containing 2% glucose (-⅋-) or 10% glucose (-◇-) and described in Example 4; and FIG. 8 shows the autoradiograph results of *A. niger* DNA digested with the following restriction enzymes: lane 2, XbaI; lane 3, XmaI; lane 4, SalI; lane 5, HindIII; lane 6, EcoRI; lane 7, BglII; lane 8, BamHI; lanes 1 and 9 contain $^{32}$P-labelled I DNA digested with BstEII. The experiment is described in Example 5.

DETAILED DESCRIPTION OF THE INVENTION

In a first aspect the invention relates to a DNA construct comprising a DNA sequence encoding a transcription factor regulating an α-amylase promoter, which DNA sequence comprises a) the transcription factor encoding part of the DNA sequence cloned into plasmid pToC320 present in *E. coli* ToC1058, DSM 10666 (SEQ ID NOS: 1 and 2), or b) an analogue of the DNA sequence defined in a), which
  i) is at least 60% homologous with the DNA sequence defined in a), or
  ii) hybridizes with the same nucleotide probe as the DNA sequence defined in a), or
  iii) encodes a transcription factor which is at least 50% homologous with the transcription factor encoded by a DNA sequence comprising the DNA sequence defined in a), or
  iv) encodes a transcription factor which is immunologically reactive with an antibody raised against the purified transcription factor encoded by the DNA sequence defined in a), or
  v) complements the mutation in ToC879, i.e. enables ToC879 to grow on cyclodextrin and produce lipase when transformed with said DNA sequence.

As defined herein, a DNA sequence analogous to the transcription factor encoding part of the DNA sequence cloned into plasmid pToC320 present in *E. coli* ToC1058, DSM 10666, is intended to indicate any DNA sequence encoding a transcription factor regulating an α-amylase promoter, which transcription factor has one or more of the properties cited under (i)–(v) above.

The analogous DNA sequence may be isolated from a strain of the filamentous fungus *A. oryzae* producing the transcription factor, or another or related organism and thus, e.g. be an allelic or species variant of the transcription factor encoding part of the DNA sequence cloned into plasmid pToC320 present in DSM 10666.

Alternatively, the analogous sequence may be constructed on the basis of the DNA sequence presented as the transcription factor encoding part of SEQ ID NO: 1 and SEQ ID NO: 2, e.g. be a sub-sequence thereof, and/or by introduction of nucleotide substitutions which do not give rise to another amino acid sequence of the transcription factor encoded by the DNA sequence, but which corresponds to the codon usage of the host organism intended for production of the transcription factor, or by introduction of nucleotide substitutions which may give rise to a different amino acid sequence.

When carrying out nucleotide substitutions, amino acid residue changes are preferably of a minor nature, that is conservative amino acid residue substitutions that do not significantly affect the folding or activity of the protein, small deletions, typically of one to about 30 amino acid residues; small amino- or carboxyl-terminal extensions.

Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine). For a general description of nucleotide substitution, see e.g. Ford, et aL., (1991), Protein Expression and Purification 2, 95–107.

It will be apparent to persons skilled in the art that such substitutions can be made outside the regions critical to the function of the molecule and still result in an active transcription factor. Amino acid residues essential to the activity of the transcription factor encoded by a DNA construct of the invention, and therefore preferably not subject to substitution, may be identified according to procedures known in the art, such as site-directed mutagenesis or alanine-scanning mutagenesis (cf. e.g. Cunningham and Wells, (1989), *Science* 244 1081–1085). In the latter technique mutations are introduced at every residue in the molecule, and the resultant mutant molecules are tested for biological activity (i.e. transcription factor regulating an α-amylase promoter) to identify amino acid residues that are critical to the activity of the molecule.

The homology referred to in (i) above is determined as the degree of identity between the two sequences indicating a derivation of the one sequence from the other. The homology may suitably be determined by means of computer programs known in the art such as GAP provided in the GCG program package (Needleman, S. B. and Wunsch, C. D., (1970), *Journal of Molecular Biology* 48 443–453). Using GAP with the following settings for DNA sequence comparison: GAP creation penalty of 5.0 and GAP extension penalty of 0.3, the coding region of the DNA sequence exhibits a degree of identity preferably of at least 60%, more preferably at least 70%, more preferably at least 80%, more preferably at least 90%, more preferably at least 95% with the transcription factor encoding part of the DNA sequence shown in SEQ ID NO: 1 and SEQ ID NO: 2.

The hybridization referred to in (ii) above is intended to indicate that the analogous DNA sequence hybridizes to the same probe as the DNA sequence encoding the transcription factor under certain specified conditions, which are described in detail in the Materials and Methods section hereinafter. The oligonucleotide probe to be used is the DNA sequence corresponding to the transcription factor encoding part of the DNA sequence shown in SEQ ID NO: 1 or SEQ ID NO: 2 or a fragment thereof.

The homology referred to in (iii) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., supra). Using GAP with the following settings for transcription factor sequence comparison: GAP creation penalty of 3.0 and GAP extension penalty of 0.1, the transcription factor encoded by an analogous DNA sequence exhibits a degree of identity preferably of at least 50%, more preferably at least 60%, more preferably at least 70%, even more preferably at least 80%, especially at least 90% with the transcription factor encoded by a DNA construct comprising the transcription factor encoding part of the DNA sequence shown in SEQ ID NO: 2, e.g. with the amino acid sequence SEQ ID NO: 3.

In connection with property (iv) the immunological reactivity may be determined by the method described in the Materials and Methods section hereinafter.

In relation to the property (v) the complementation method is described in Example 1 herein.

The DNA sequence encoding a transcription factor of the invention can be isolated from the strain *Aspergillus oryzae* IFO 4177 using standard methods e.g. as described by Sambrook, et al., (1989) Molecular Cloning: A Laboratory Manual. Cold Spring Harbor Lab.; Cold Spring Harbor, N.Y.

General RNA and DNA isolation methods are also disclosed in WO 93/11249 and WO 94/14953, the contents of which are hereby incorporated by reference. A more detailed description of the complementation method is given in Example 1 herein.

Alternatively, the DNA encoding a transcription factor of the invention may, in accordance with well-known procedures, be conveniently isolated from a suitable source, such as any of the below mentioned organisms, by use of synthetic oligonucleotide probes prepared on the basis of a DNA sequence disclosed herein. For instance, a suitable oligonucleotide probe may be prepared on the basis of the transcription factor encoding part of the nucleotide sequences presented as SEQ ID NO: 1 or any suitable subsequence thereof, or on the basis of the amino acid sequence SEQ ID NO: 3.

The invention relates specifically to a transcription factor regulating the expression of the α-amylase promoter in a filamentous fungus, which factor as indicated in Example 2 may even regulate the expression of other genes.

In this context the expression "filamentous fungus" is intended to include the groups Phycomycetes, Zygomycetes, Ascomycetes, Basidiomycetes and fungi imperfecti, including Hyphomycetes such as the genera Aspergillus, Penicillium, Trichoderma, Fusarium and Humicola.

In this context the expression "α-amylase promoter" means a sequence of bases immediately upstream from an α-amylase gene which RNA polymerase recognises and binds to promoting transcription of the gene coding for the α-amylase.

As indicated, transcription factors are known from many organisms and it is therefore expected that similar or corresponding factors may be found originating from other fungi of the genera Aspergillus, Trichoderma, Penicillium, Fusarium, Humicola, etc., having an enhancing effect on the expression of a polypeptide being under the regulation of amylase promoters in any fungus belonging to any of these genera.

A comparison of the DNA sequence coding for the transcription factor regulating the α-amylase promoter has shown some degree of homology to a transcription factor (CASUCI) regulating the expression of glucosidase in Candida and to MAL63 of *Saccharomyces cerevisiae* as disclosed in Kelly and Kwon-Chung, (1992) *J. Bacteriol.* 174 222–232.

It is at present contemplated that a DNA sequence encoding a transcription factor homologous to the transcription factor of the invention, i.e. an analogous DNA sequence, may be obtained from other microorganisms. For instance, the DNA sequence may be derived by a similar screening of a cDNA library of another microorganism, such as a strain of Aspergillus, Saccharomyces, Erwinia, Fusarium or Trichoderma.

An isolate of a strain of *A. oryzae* from which the gene coding for a transcription factor of the invention has been inactivated has been deposited by the inventors according to the Budapest Treaty on the International Recognition of the Deposit of Microorganisms for the Purposes of Patent Procedure at the DSM, Deutsche Sammlung von Mikroorganismen und Zellkulturen GmbH, Mascheroder Weg 1b, D-38124 Braunschweig, DEUTSCHLAND.

Deposit date: MAY 6, 1996 (May 6, 1996)
Depositor's ref.: ToC879=NN049238
DSM designation: *Aspergillus oryzae* DSM No.10671

The deposited strain *Aspergillus oryzae* DSM No.10671 can be used to isolate a transcription factor according to the invention from any strain of *Aspergillus oryzae* and any other fungal strain having such a gene by complementation as described hereinafter.

The expression plasmid pToC320 comprising the full length genomic DNA sequence encoding the transcription factor of the invention has been transformed into a strain of *E. coli* resulting in the strain ToC1058, which has been deposited by the inventors according to the Budapest Treaty on the International Recognition of the Deposit of Microorganisms for the Purposes of Patent Procedure at the DSMZ, Deutsche Sammlung von Mikroorganismen und Zellkulturen GmbH., Mascheroder Weg 1b, D-38124 Braunschweig, DEUTSCHLAND.

Deposit date: MAY 6, 1996 (May 6, 1996)
Depositor's ref.: ToC1058=NN049237
DSM designation: *E. coli* DSM No.10666

According to the invention, factors of this type originating from the species *A. oryzae, A. niger, A. awamori,* etc., especially *A. oryzae* IFO4177 are preferred.

The transcription factor of the invention has been found not only to be involved in the regulation of the α-amylase promoter, but also in the regulation of the glucoamylase promoter from *A. oryzae*.

Especially, the invention comprises any factor having an amino acid sequence comprising one or more fragments or combinations of fragments of the amino acid sequence depicted as SEQ ID NO: 3.

Truncated forms of the transcription factor may also be active. By truncated forms are meant modifications of the transcription factor wherein N-terminal, C-terminal or one or more internal fragments have been deleted.

A further aspect of the invention relates to a DNA sequence coding for any of these factors.

In this aspect the invention especially comprises any DNA sequence coding for one or more fragments of the amino acid sequence depicted as SEQ ID NO: 3.

More specifically the invention relates to a DNA sequence comprising one or more fragments or a combination of fragments of the DNA sequence depicted as SEQ ID NO: 1 and SEQ ID NO: 2.

According to a further aspect the invention relates to a method of producing a filamentous fungal host cell comprising the introduction of any of the above mentioned DNA fragments into a filamentous fungus wherein the α-amylase promoter or another co-regulated promoter regulates the expression of a polypeptide of interest in a manner whereby said factor will be expressed in said fungus.

The introduction of said DNA fragment may be performed by means of any well known standard method for the introduction of DNA into a filamentous fungus, such as by use of an expression vector and host cells as described below.

Therefore, the invention also provides a recombinant expression vector comprising the DNA construct of the invention.

The expression vector of the invention may be any expression vector that is conveniently subjected to recombinant DNA procedures, and the choice of vector will often depend on the host cell into which it is to be introduced.

Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the expression vector, the DNA sequence encoding the transcription factor should either also contain the expression signal normally associated with the transcription factor or should be operably connected to a suitable promoter and terminator sequence. The promoter may be any DNA sequence which shows transcriptional activity in the host cell of choice and may be derived from genes that are either homologous or heterologous to the host cell. The procedures used to ligate the DNA sequences coding for the transcription factor, the promoter and the terminator, respectively, and to insert them into suitable vectors are well known to persons skilled in the art (cf., Sambrook, et al., supra).

Examples of suitable promoters for use in filamentous fungal host cells are, for instance, the *A. nidulans* ADH3 promoter (McKnight, et al. (1985) The *EMBO J.* 4 2093–2099) or the tpiA promoter. Examples of other useful promoters are those derived from the gene encoding *Aspergillus oryzae* α-amylase, *Aspergillus niger* neutral alpha-amylase, *Aspergillus niger* acid stable alpha-amylase, *Aspergillus niger, Aspergillus awamori,* or *Aspergillus. oryzae* glucoamylase (gluA), *A. oryzae* alkaline protease (alp), *A. oryzae* nitrate reductase (niaD), *Aspergillus oryzae* triose phosphate isomerase (tpi), *Aspergillus nidulans* acetamidase, or an Aspergillus promoter coding for an amino acid biosynthetic gene such as argB.

In yet another aspect the invention provides a host cell comprising the DNA construct of the invention and/or the recombinant expression vector of the invention.

Preferably, the host cell of the invention is a eukaryotic cell, in particular a fungal cell such as a yeast or filamentous fungal cell. In particular, the cell may belong to a species of Trichoderma, preferably *Trichoderma harzianum* or *Trichoderma reesei,* or a species of Aspergillus, most preferably *Aspergillus oryzae* or *Aspergillus niger.* Fungal cells may be transformed by a process involving protoplast formation and transformation of the protoplasts followed by regeneration of the cell wall in a manner known per se. The use of Aspergillus as a host microorganism is described in EP 238 023 (Novo Nordisk A/S), the contents of which are hereby incorporated by reference. The host cell may also be a yeast cell, e.g. a strain of Saccharomyces, in particular *Saccharomyces cerevisiae, Saccharomyces kluyveri* or *Saccharomyces uvarum,* a strain of Schizosaccharomyces sp., such as *Schizosaccharomyces pombe,* a strain of Hansenula sp., Pichia sp., Yarrowia sp., such as *Yarrowia lipolytica,* or Kluyveromyces sp., such as *Kluyveromyces lactis.*

The endogenous amyR gene of the host cell may be deleted or inactivated by other means. The introduction of amyR control by a heterologous promoter will then lead to a completely new scheme of regulation of the alpha-amylase promoter. If, for example, amyR is fused to the *A. oryzae* niaD promoter, the alpha-amylase promoter will become inducible by nitrate. If, instead of the niaD promoter, a palC-regulated promoter is used, the activity of the alpha-amylase promoter will be regulated by pH.

The invention also comprises a method of producing a polypeptide of interest, whereby a host cell as described above is grown under conditions conducive to the production of said factor and said polypeptide of interest, and said polypeptide of interest is recovered.

The medium used to culture the transformed host cells may be any conventional medium suitable for growing the host cells in question. The expressed polypeptide of interest may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

According to the invention the method may be used to produce a polypeptide of interest that is a medicinal polypeptide, especially such medicinal polypeptides as growth hormone, insulin, blood clotting factor, and the like.

The method of the invention may also be used for the production of industrial enzymes, such as proteases, lipases, amylases, glucoamylases, oxido reductases, carbohydrases, carbonyl hydrolases, cellulases, esterases, etc.

According to a further aspect of the invention said transcription factor may be used for enhancing the expression of a polypeptide of interest in a filamentous fungus, such as a fungus of the genus Aspergillus, Trichoderma, Penicillium, Fusarium, Humicola, etc., especially of the species *A. oryzae, A. niger, A. awamori,* etc., and specifically *A. oryzae.*

The transcription factor of the invention may thus be used to enhance the expression of a medicinal polypeptide, such as growth hormone, insulin, blood clotting factor, etc.

Also, the expression of industrial enzymes, such as proteases, lipases, amylases, glucoamylases, oxido reductases, carbohydrases, carbonyl hydrolases, cellulases, esterases, etc., may be enhanced by the use of the transcription factor of the invention.

The transcription factor may also be used to identify the sequences in the alpha-amylase promoter to which it binds. For example, this could be done by making a GST-fusion protein with the DNA binding domain of AmyR, such as the zinc finger, for production in *E. coli*. Such fusion proteins may be conveniently made using commercially available kits, for example, "The GST Gene Fusion Kit" from Pharmacia. The purified GST-fusion protein can then be used in conventional in vitro techniques such as gel shift assays or DNA footprint analyses (Kulmburg, P., et al. (1992) Molecular and Cellular Biology 12 1932–1939; Lutfiyya, L. L., and Johnston, M. (1996) Molecular and Cellular Biology 16 4790–4797). The identification of the AmyR binding site will make it possible to insert these sequences in other promoters not normally regulated by AmyR.

Materials and Methods

Hybridization

Suitable hybridization conditions for determining hybridization between a nucleotide probe and an "analogous" DNA sequence of the invention may be defined as described below. The oligonucleotide probe to be used is the DNA sequence corresponding to the transcription factor encoding part of the DNA sequence shown in SEQ ID NO: 1, i.e. nucleotides 1691..2676+2743..3193+3278..3653 in SEQ ID NO: 1, or a fragment thereof, e.g. nucleotides 1770–1800 in SEQ ID NO: 1.

Hybridization Conditions

Suitable conditions for determining hybridization between a nucleotide probe and a homologous DNA or RNA sequence involves pre-soaking of the filter containing the DNA fragments or RNA to hybridize in 5×SSC (standard saline citrate buffer) for 10 min, and prehybridization of the filter in a solution of 5×SSC (Sambrook, et al., supra), 5×Denhardt's solution (Sambrook, et al., supra), 0.5% SDS and 100 µg/ml of denatured sonicated salmon sperm DNA (Sambrook, et al., supra), followed by hybridization in the same solution containing a random-primed (Feinberg, A. P. and Vogelstein, B. (1983) *Anal. Biochem.* 132 6–13), $^{32}P$-dATP-labeled (specific activity>$1\times10^9$ cpm/µg) probe for 12 hours at ca. 65° C. The filter is then washed two times for 30 minutes in 2×SSC, 0.5% SDS at preferably not higher than 50° C., more preferably not higher than 55° C., more preferably not higher than 60° C., more preferably not higher than 65° C., even more preferably not higher than 70° C., especially not higher than 75° C.

Molecules to which the nucleotide probe hybridizes under these conditions are detected using a Phospho Image detector.

Immunological Cross-reactivity

Antibodies to be used in determining immunological cross-reactivity may be prepared by use of a purified transcription factor. More specifically, antiserum against the transcription factor of the invention may be raised by immunizing rabbits (or rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically pp. 27–31). Purified immunoglobulins may be obtained from the antisera, for example by salt precipitation ($(NH_4)_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, ed.), Blackwell Scientific Publications, 1967, pp.655–706), by crossed immunoelectrophoresis (N. Axelsen et al., supra, Chapters 3 and 4), or by rocket immunoelectrophoresis (N. Axelsen et al., op cit., Chapter 2).

EXAMPLES

Example 1

Cloning of the amyR Transcription Factor from *A. oryzae* amyR was cloned by complementation of an *A. oryzae* mutant strain unable to express two different proteins both under control of the TAKA-amylase promoter. The mutant *A. oryzae* strain ToC879 was made by mutagenesis of a strain, SRe440, containing a lipase (HLL) encoding cDNA under control of the TAKA promoter and one copy of the TAKA-amylase gene transcribed from its own promoter.

The mutant was identified and isolated by its amylase negative (amylase$^-$) phenotype and subsequently shown to be lipase negative (lipase$^-$) as well.

The strain ToC879 contains intact copies of both expression cassettes. The amylase$^-$ phenotype makes ToC879 unable to grow on plates containing 1% cyclodextrin as the sole carbon source, while the parent strain SRe440 will grow on such plates.

ToC879 has been deposited at DSM under the name DSM No.10671.

amyR was isolated by co-transforming ToC879 with an *A. oryzae* cosmid library and an autonomously replicating pHelp1 based plasmid (D. Gems, I. L. Johnstone, and A. J. Clutterbuck (1991) *Gene* 98 61–67) carrying the bar gene from *Streptomyces hygroscopicus* which confers resistance to glufosinate. The transformants were subjected to selection on plates containing cyclodextrin as the sole carbon source and screened for a concurrent reversion to the lipase$^+$ phenotype.

The transforming DNA was rescued from colonies able to grow on cyclodextrin. Subcloning resulted in the isolation of a 4.3 kb DNA fragment able to complement both phenotypes of ToC879. The gene harboured on this fragment was named amyR.

Construction of the pHelp1 Derivative pMT1657Construction of the pHelp1 Derivative pMT1657.Construction of the pHelp1 Derivative pMT1657.

A plasmid, pMT1612, was made by ligation (and subsequent transformation into *E. coli* DH5a) of the following four fragments:

i) the *E. coli* vector pToC65 (described in EP 531 372) cut with SphI/XbaI,
ii) a PCR fragment (containing the *A. nidulans* amdS promoter) cut with SphI/BamHI,
iii) a 0.5 kb BamHI/XhoI fragment from pBP1T (B. Staubinger et al., (1992) *Fungal Genetics Newsletter* 39 82–83) containing the bar gene, and
iv) a 0.7 kb XhoI/XbaI fragment from pIC AMG/Term (EP Application No. 87103806.3) containing the *A. niger* glucoamylase transcription terminator.

The PCR fragment containing the amdS promoter was made using the plasmid pMSX-6B1 (M. E. Katz et al., (1990) *Mol. Gen. Genet.* 220 373–376) as substrate DNA and the two oligonucleotides 4650 (SEQ ID NO: 4) and 4561 (SEQ ID NO: 5) as primers.

Figure 1:
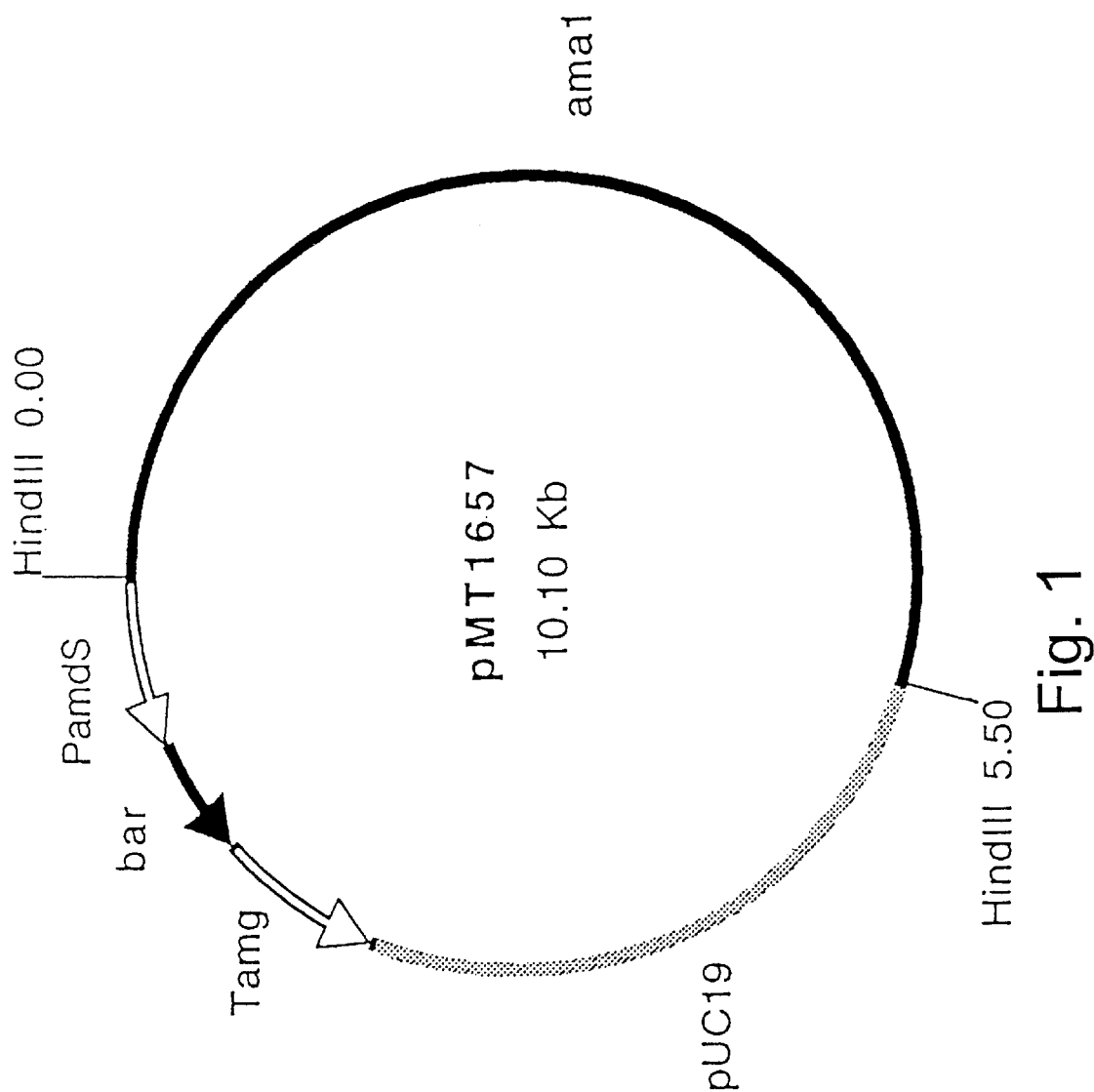
FIG. 1 shows the structure of the plasmid pMT1657, the construction of which is described in Example 1.

4650: CTTGCATGCCGCCAGGACCGAGCAAG, SEQ ID NO: 4
4651: CTTGGATCCTCTGTGTTAGCTTATAG. SEQ ID NO: 5 pMSX-6B1 contains an amdS promoter up mutation called 1666. pMT1612 was cut with HindIII, dephosphorylated and ligated to a 5.5 kb HindIII fragment from pHelp1 containing the AMA1 sequence. The resulting plasmid, pMT1657 is self-replicating in Aspergilli and can be selected for by increased resistance to glufosinate. pMT1657 is depicted in FIG. 1, wherein PamdS represents the amdS promoter of fragment ii) above, bar represents fragment iii) above, and Tamg represents fragment iv) above.

Construction of the Cosmid LibraryConstruction of the Cosmid Library

A cosmid library of Aspergillus oryzae was constructed essentially according to the instructions from the supplier of the "SuperCos1 cosmid vector kit" (Stratagene Cloning Systems, La Jolla Calif., USA).

Genomic DNA of A. oryzae IFO4177 was prepared from protoplasts made by standard procedures (Christensen, T., et al. (1988) Biotechnology 6 1419–1422).

After isolation the protoplasts were pelleted by centrifugation at 2500 rpm for 5 minutes in a Labofuge T (Heto); the pellet was then suspended in 10 mM NaCl, 20 mM Tris-HCl (pH 8.0), 1 mM EDTA, 100 µg/ml proteinase K and 0.5% SDS as stated in the manual from the Supercos 1 cosmid vector kit; the rest of the DNA preparation was done according to the instructions of the kit.

The size of the genomic DNA was analysed by electrophoresis using the CHEF-gel apparatus (Bio-Rad Laboratories, Hercules Calif., USA). A 1% agarose gel was run for 20 hours at 200 volts with a 10–50 second pulse. The gel was stained with ethidium bromide and photographed. The DNA was 50→100 kb in size. The DNA was partially digested using Sau3A.

The size of the digested DNA was 20–50 kb determined by the same type of CHEF-gel analysis as above. The CsCl gradient banded SuperCos1 vector was prepared according to the manual. Ligation and packaging were likewise performed as described in the manual.

After titration of the library, all of the packaging mix from one ligation and packaging was transfected into the host cells, XL1-Blue MR, and plated on 50 µg/ml ampicillin LB plates. Approximately 3800 colonies were obtained. Cosmid preparations from 10 colonies showed that they all had inserts of the expected size. The colonies were picked individually and inoculated in microtiter plate wells with 100 µl LB (100 µg/ml ampicillin) and incubated at 37° C. overnight. 100 µl of 50% glycerol was added to each well, and the entire library was frozen at −80° C. A total of 3822 colonies were stored.

This represents the A. oryzae genome approximately 4.4 times. After picking the colonies the plates were scraped off, the scrape-off pooled and the total library was also stored in four pools as frozen glycerol stock. The four pools were named ToC901 –ToC904.

The individually frozen colonies in the library were inoculated onto LB-plates (100 µg/ml ampicillin) by using a multipin device of 6 rows of 8 pins fitting into half a microtiter dish. Plates were made containing colonies from all clones in the library.

The plates were incubated at 37° C. overnight. Sterilized Whatman 540 filters cut to the size of a petri dish were placed upon the colonies which were incubated for two more hours at 37° C. The filters were transferred to LB plates containing 200 µg/ml of chloramphenicol and the plates were incubated overnight at 37° C.

The next day the filters were washed twice in 0.5 M NaOH for 5 minutes, then twice in 0.5 M Tris-HCl (pH7.4) for 5 minutes and then twice in 2×SSC for 5 minutes. The filters were wetted with ethanol and air dried.

Selection of amyR ClonesSelection of amyR Clones

Cosmid DNA was prepared from ToC901–904 and introduced into ToC879 by co-transformation with pMT1657. The transformation procedure is described in EP Application No. 87103806.3. Approximately 8700 transformants were selected by resistance to 1 mg/ml glufosinate in minimal plates (Cove D. J. (1966) BBA 113 51–56) containing 1 M sucrose for osmotic stabilization and 10 mM $(NH_4)_2SO_4$.

Ten randomly chosen transformants were reisolated once on the same type of plates. Conidiospores from these 10 transformants were inoculated in minimal medium containing 1 mg/ml glufosinate and grown at 30° C. until enough mycelium for DNA preparation could be harvested. DNA was prepared as described in T. Christensen et al. (supra).

The uncut DNA was applied to a 0.7% agarose gel, and electrophoresis was performed, followed by Southern blotting. The blot was hybridized with a $^{32}$P-labelled SuperCos1 specific DNA fragment. Each of the ten transformants showed a band with a higher mobility than the linear chromosomal DNA. Each of the bands also hybridized to a pHelp1 specific probe, indicating that the co-transformation frequency of the cosmid library was close to 100% and that the cosmids had integrated into the autonomously replication vector pHelp1.

The transformants were unstable as expected for pHelp1 transformants. Less than 10% of the conidiospores from a glufosinate resistant colony gave rise to glufosinate-resistant progeny.

Conidiospores from all the transformants were collected in 8 pools and plated on minimal plates (Cove D. J., supra) containing 1 mg/ml glufosinate, 10 mM $(NH_4)_2SO_4$ and 1% b-cyclodextrin (Kleptose from Roquette Frères, 62136 Lestem, France)

Four colonies were obtained from one of the pools and one from one of the other pools. Two of the colonies from the first pool were reisolated once on the same kind of plates.

Conidiospores from the reisolated colonies were plated on minimal plates with either glucose or cyclodextrin as a carbon source and on glufosinate-containing plates. The glufosinate resistance and the ability to grow on cyclodextrin were both unstable phenotypes with the same degree of instability. This indicated that the gene conferring the ability to grow on cyclodextrin was physically linked to pMT1657 in the transformants.

Colonies from the reisolation plates were cut out and were analysed by rocket immune electrophoresis (RIE) using an antibody raised against the HLL lipase. The transformants gave a clear reaction with the antibody, while ToC879 colonies grown on maltose gave no reaction. This led to the conclusion that both the expression of amylase (i.e., growth on cyclodextrin) and lipase (i.e. antibody binding) had been restored in these transformants. The gene responsible for this phenotype was named amyR.

Isolation of the amyR Gene

In order to rescue the amyR gene from the amylase$^+$, lipase$^+$ transformants of ToC879, two different approaches were used successfully.

DNA was prepared from mycelium grown in minimal medium with cyclodextrin as the carbon source.

In the first approach the DNA was packaged into λ-heads using the Gigapack® II kit from Stratagene in an attempt to rescue the original cosmid out of the total DNA. The packaging reaction was incubated with XL1-Blue MR E.

coli under the conditions specified by the kit supplier. The *E. coli* cells were plated on LB plates with 50 μg/ml ampicillin. Two colonies appeared on the plates; the cosmids they contained were identical and named ToC1012.

In the second approach the total DNA was used in an attempt to transform competent *E. coli* DH5a cells. Sixteen colonies were isolated and shown to contain six different plasmids by restriction enzyme digest. Each of the plasmids was digested with EcoRI and subjected to Southern analysis. A $^{32}$P-labelled probe of a mixture of pMT1657 and Super-Cos1 was used to identify DNA fragments not part of any of these vectors. Two EcoRI fragments, approximately 0.7 and 1.2 kb in size, did not hybridize to any of these probes. The 1.2 kb fragment was isolated, labelled with $^{32}$P and used as a probe in a hybridization experiment with the filters containing the part of the cosmid library that gave rise to the original transformants. Six cosmids from the pool (ToC904), containing approximately 1000 clones did hybridize.

Of these, some were shown by restriction enzyme digestion to be identical, resulting in the isolation of four different cosmids. All cosmids contained at least parts of the TAKA-amylase gene as well. The four cosmids and the cosmid ToC1012 were transformed into ToC879 by co-transformation with pMT1623, a pUC based plasmid that carries the bar gene under the control of the *A. oryzae* tpi promoter. Fifteen transformants from each co-transformation were isolated by resistance to glufosinate and tested for the ability to grow on cyclodextrin.

Eight transformants of ToC1012 and three transformants of one of the other cosmids, 41B12, were able to grow. None of the transformants of the other cosmids grew. That not all of the transformants of ToC1012 and 41B12 were able to grow is likely to be a reflection of the co-transformation frequency in each experiment. Colonies from the transformants growing on cyclodextrin were analysed by RIE, and showed that they all produced lipase.

Figure 2:
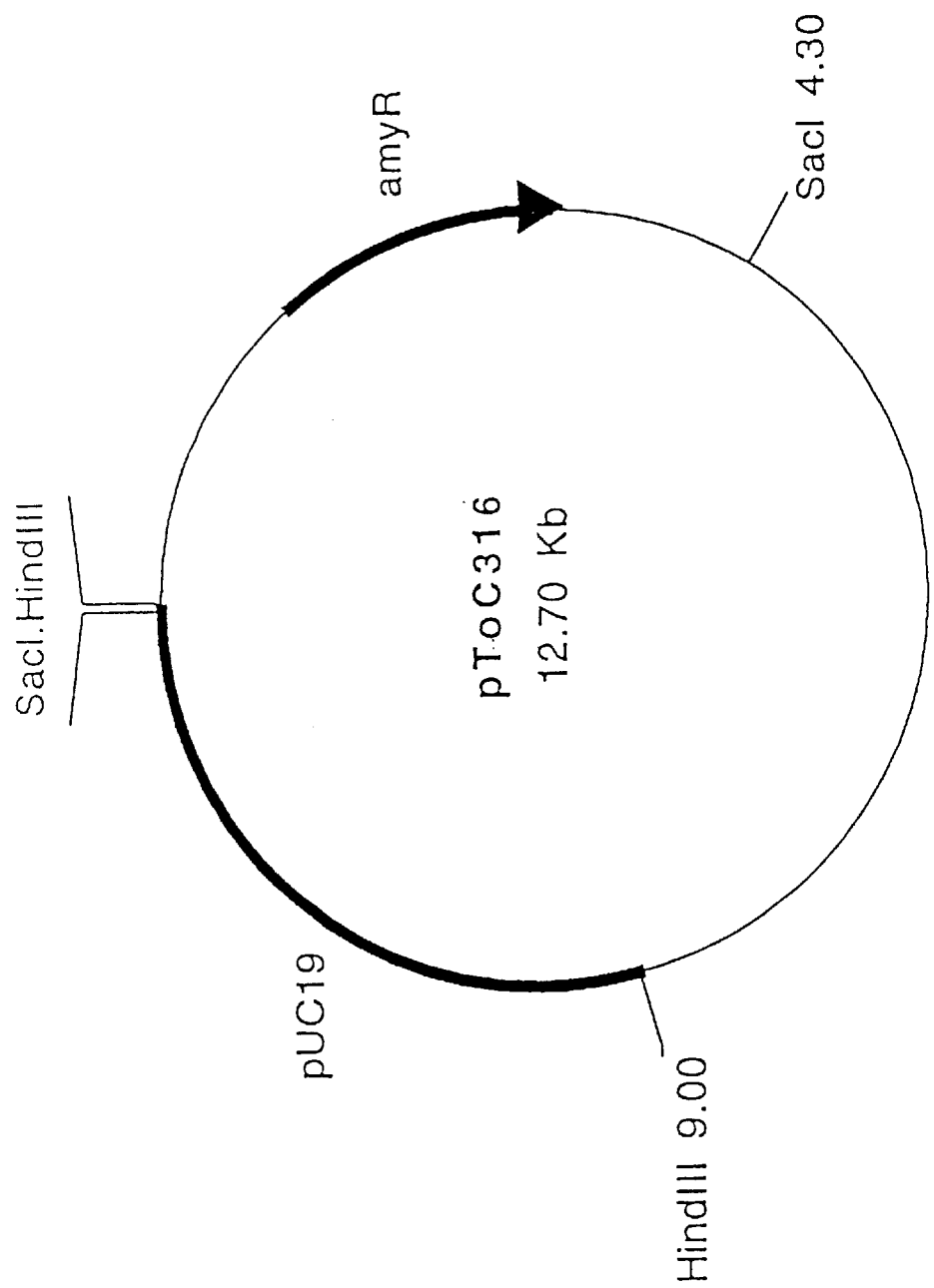
FIG. 2 shows the structure of the plasmid pToC316, the construction of which is described in Example 1.

DNA fragments obtained by digesting 41 B12 with either BgIll, HindIII or PstI were cloned into pUC19 in order to subclone amyR from the cosmid. The subclones were transformed into ToC879 and the transformants analysed for the ability to grow on cyclodextrin and produce lipase as described above. As depicted in FIG. 2, one plasmid called pToC316 was shown to contain an approximate 9 kb HindIII fragment which was identified as containing amyR.

Figure 3:
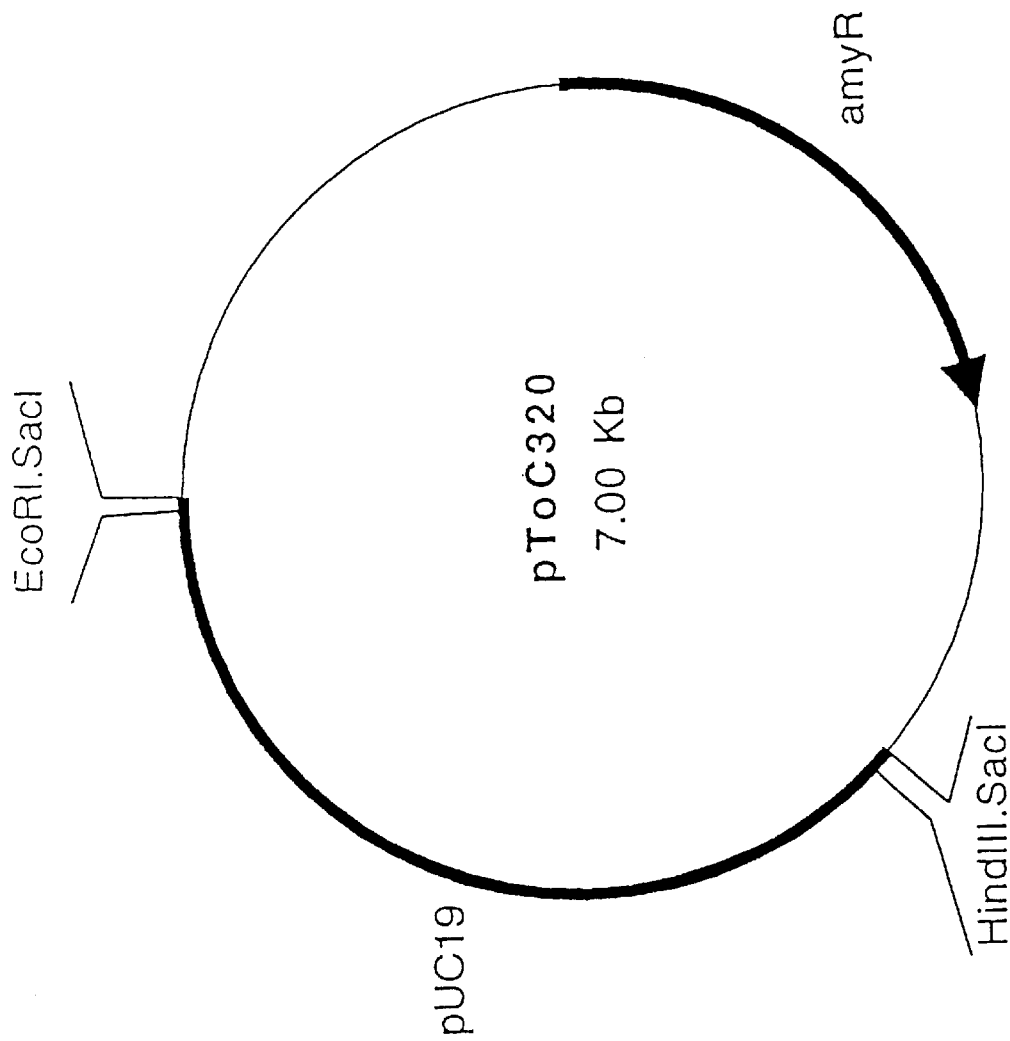
FIG. 3 shows the structure of the plasmid pToC320, the construction of which is described in Example 1.

Further subcloning resulted in a plasmid called pToC320 containing a 4.3 kb HindIII/SacI fragment, which is shown in FIG. 3 and was subsequently sequenced on an ABI DNA sequencer using both further subcloning and primer walking.

A DNA sequence of 3980 bp including the amyR gene is shown in SEQ ID NO: 1. The deduced amino acid sequence is shown in SEQ ID NO: 3 and reveals a Gal 4-type zinc finger sequence between amino acids 28–54. Such sequences are known to bind to DNA (Reece, R. J., and Ptashne, M. (1993) Science 261 909–910).

amyR maps close to one of the three amylase genes in IFO4177, since it was isolated from a cosmid also containing amylase-specific DNA fragments. Mapping of the cosmid showed that the α-amylase gene and amyR are 5–6 kb apart. Southern analysis of genomic DNA showed that only one copy of amyR is present in IFO4177, and confirmed that it maps close to one of the amylase genes.

Analysis of amyR cDNA mRNA was made by the method of Wahleithner, J. A., et al. (1996, *Curr. Genet* 29 395–403) from a culture of *A. oryzae* grown in maltose containing medium under conditions favorable for α-amylase production. Double stranded cDNA was made by standard procedures and used for PCR reactions with the following primers:

```
oligodT primer:
TTTTGTAAGCT₃₁                         SEQ ID NO: 9
23087:
CCCCAAGCTTCGCCGTCTGCGCTGCTGCCG        SEQ ID NO: 6
20865:
CGGAATTCATCAACCTCATCAACGTCTTC         SEQ ID NO: 7
20866:
CGGAATTCATCGGCGAGATAGTATCCTAT         SEQ ID NO: 8
```

A PCR reaction with the primers 20866 and 23087 resulted in a fragment of approximately 1.1 kb. The fragment was digested with EcoRI and HindIII; these restriction sites were incorporated into the primers, and cloned into a pUC19 vector cut with the same enzymes.

The insert in the resulting plasmid was sequenced, the result located one intron in this part of the gene. The intron is indicated in SEQ ID NO: 2.

Another PCR reaction with the oligodT primer and primer 20866 did not result in a distinct fragment. An aliquot of this reaction was used as the starting point for a new reaction with the oligodT primer and the primer 20865, which resulted in a fragment of approximately 1.1 kb. This fragment was digested with EcoRI and HindIII and cloned into pUC19.

Sequencing showed that the fragment contained the 3' part of amyR and another intron was located. This is also indicated in SEQ ID NO: 2. Three independent plasmids were sequenced at the 3' end and two polyA addition sites were located, one at bp no. 3827 and one at bp no. 3927.

Example 2

Quantification of Glucoamylase Synthesis in an amyR Strain

*A. oryzae* produces a glucoamylase, encoded by the gIaA gene, which is regulated by the same substances as α-amylase (Y. Hata et al.(1992) *Curr. Genet.* 22 85–91). In order to see whether amyR is also involved in regulation of gIaA the synthesis of glucoamylase was measured under inducing conditions in the amyR strain ToC879 and in the amyR wt strain SRe440, from which ToC879 was directly derived.

Conidiospores from each strain were inoculated in 10 ml YPM (YP containing 2% maltose) and grown for four days at 30° C. Supernatants were collected and analysed for glucoamylase content by incubation with p-nitrophenyl a-D-glucopyranoside, a substrate that turns yellow when cleaved by glucoamylase. In the procedure used, 0.5 ml of fermentation broth was mixed with 1 ml of 0.1 M Na-acetate pH=4.3, containing 1 mg/ml of the substrate. The samples were incubated for 3 hours at room temperature and 1.5 ml of 0.1 M $Na_2B_4O_7$ was added. The yellow colour was measured in a spectrophotometer at 400 nm. Control samples were made by mixing the supernatants first with the borate and then with the substrate solution. The results were:

| | reaction-control (OD units) |
|---|---|
| SRe440 | 0.655 |
| ToC879 | 0.000 |

The absence of any OD reading in the sample taken from ToC879 clearly indicate that synthesis of glucoamylase of *A. oryzae* requires the expression of the AmyR transcription factor.

Example 3
Overexpression of AmyR

A plasmid, pToC342, containing the coding region and 3' noncoding sequences of amyR fused to the promoter for the A. oryzae tpi gene was constructed. The tpi gene codes for triosephosphate isomerase, a constitutively expressed enzyme involved in primary metabolism. The A. oryzae tpi gene was isolated by crosshybridization with an A. nidulans cDNA clone according to the procedure of McKnight, G. L., et al, (1986, Cell 46 143–147). Sequencing led to identification of the structural gene. The promoter used was a fragment of approximately 700 bp immediately upstream of the coding region. pToC342 was able to complement the mutation in ToC879. To pToC342 was further added the A. oryzae pyrG gene and the resulting plasmid, pToC359, was transformed into JaL250, a pyrG mutant of JaL228 described in patent application DK1024/96 filed Sep. 19, 1996. Strains containing multiple copies of pToC359 were found to synthesise increased levels of glucoamylase.

Construction of pToC342 and pToC359

A PCR reaction was made with pToC320 as the template and the following primers:

```
8753    GTTTCGAGTATGTGGATTCC            (SEQ ID NO:10)

8997    CGGAATTCGGATCCGAGCATGTCTCATTCTC (SEQ ID NO:11)
```

Figure 4:
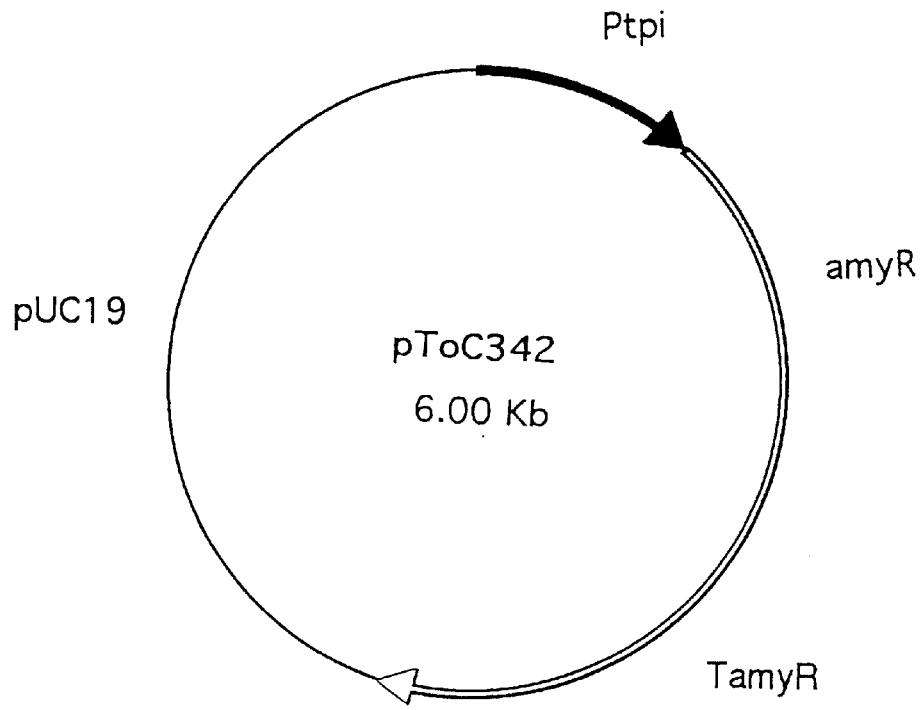
FIG. 4 shows the structure of the plasmids pToC342 and pToC359, the construction of which are described in Example 3.
Figure 4:
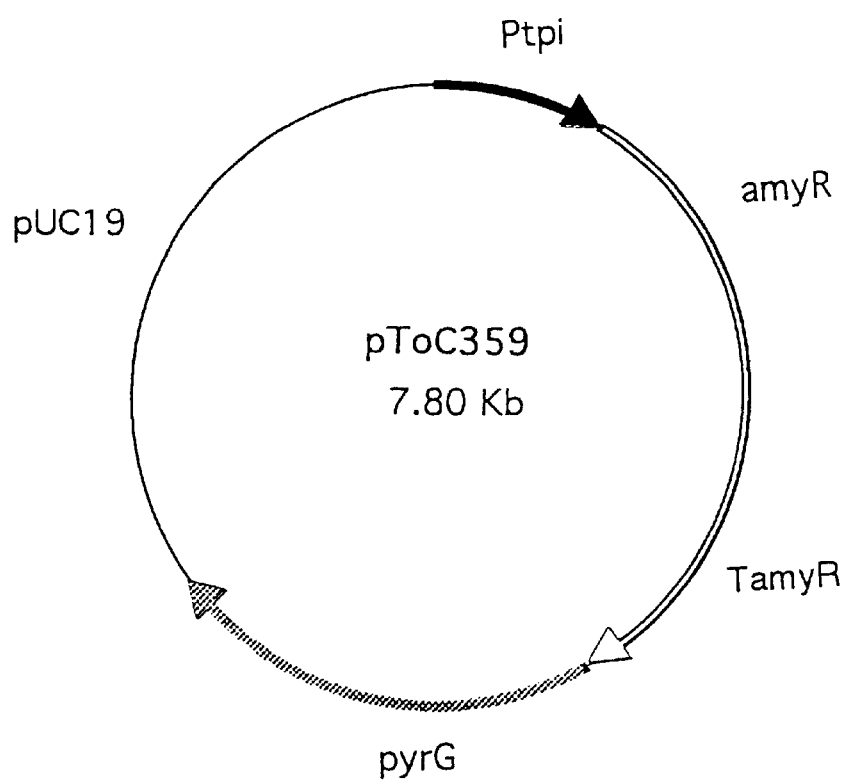

The resulting fragment was cut with EcoRI/ApaI to produce a fragment of approximately 180 bp which was then cloned into pToC320 that had been digested with EcoRI/ApaI. The resulting plasmid, pToC336, was sequenced to confirm that the PCR fragment was intact. The 2.6 kb BamHI/SacI fragment of pToC336 containing the coding region and the 3' untranslated sequence of amyR and an EcoRI/BamHI fragment of approximately 700 bp containing the tpi promoter was cloned into EcoRI/SacI digested pUC19. The BamHI site downstream of the tpi promoter was introduced in vitro, whereas the EcoRI site is an endogenous site from the original tpi clone. The resulting plasmid, called pToC342, was cut with HindIII, dephosphorylated and ligated to a 1.8 kb HindIII fragment containing the A. oryzae pyrG gene, resulting in a plasmid which was called pToC359. The structure of both pToC342 and pToC359 are shown in FIG. 4, wherein Ptpi represents the tpi promoter and TamyR represents the 3' noncoding region of amyR. The cloning of the pyrG gene has been previously described in WO 95/35385.

Expression in A. oryzae JaL250

JaL250 is a pyrG mutant of JaL228 selected by resistance to 5-fluoro-orotic acid. JaL228 has been described in patent application DK1024/96 filed Sep. 19, 1996. JaL250 was transformed with pToC359 using standard procedures and by selecting for relief of uridine requirement. The transformants were reisolated twice through conidiospores and grown for four days in YP+2% maltose at 30° C. Secreted glucoamylase was measured by the ability to cleave p-nitrophenyl a-D-gluco-pyranoside. The transformants had 5–31 arbitrary glucoamylase units/ml in the fermentation broth, while JaL228 had 2–3 units/ml. The best transformant was named ToC1200. Southern analysis showed that multiple copies of pToC359 had integrated into the genome of ToC1200. Because of the alpha-amylase promoter, ToC1200 may be used advantageously as a host strain for expression plasmids.

Example 4
Carbon Catabolite Repression of the TAKA-promoter

The TAKA-amylase promoter is subject to carbon catabolite repression. In Aspergilli carbon catabolite repression is at least partially mediated via the transcriptional repressor CreA, a homologue to S. cerevisiae MIG1. The DNA binding sites in promoters under CreA control are known to be GC-rich and seemingly identical to the MIG1 sites in S. cerevisiae. The TAKA-amylase promoter contains several potential CreA binding sites. To determine whether this promoter is involved in carbon catabolite repression, three such sites were mutated, but provided only partial relief of carbon catabolite repression. In contrast, introduction of copies of constitutively expressed AmyR in strains containing the modified promoter coupled to a reporter gene completely relieved repression of the reporter.

Construction of a CreA Site Deleted TAKA-amylase Promoter

Three sites were identified as being potential CreA binding sites in the TAKA-amylase promoter by sequence comparison to known CreA and MIG1 sites. The resulting sites have the following sequences:

```
Site I      CCCCGGTATTG    (SEQ ID NO: 12)
Site II     CCCCGGAGTCA    (SEQ ID NO: 13)
Site III    ATATGGCGGGT    (SEQ ID NO: 14)
```

The bases underlined were changed to A's because such changes are known to destroy MIG1 binding sites. The substitutions were made using standard site-specific mutagenesis procedures. An expression vector, pToC297, containing the modified promoter and the 3' nontranscribed sequence of the glucoamylase gene from A. niger was constructed. pToC297 is identical to pToC68 described in WO 91/17243 except for the changes in the promoter. Both plasmids have a unique BamHI site between the promoter and the terminator.

Expression of a Lipase Regulated by a CreA TAKA-amylase Promoter

Figure 5:
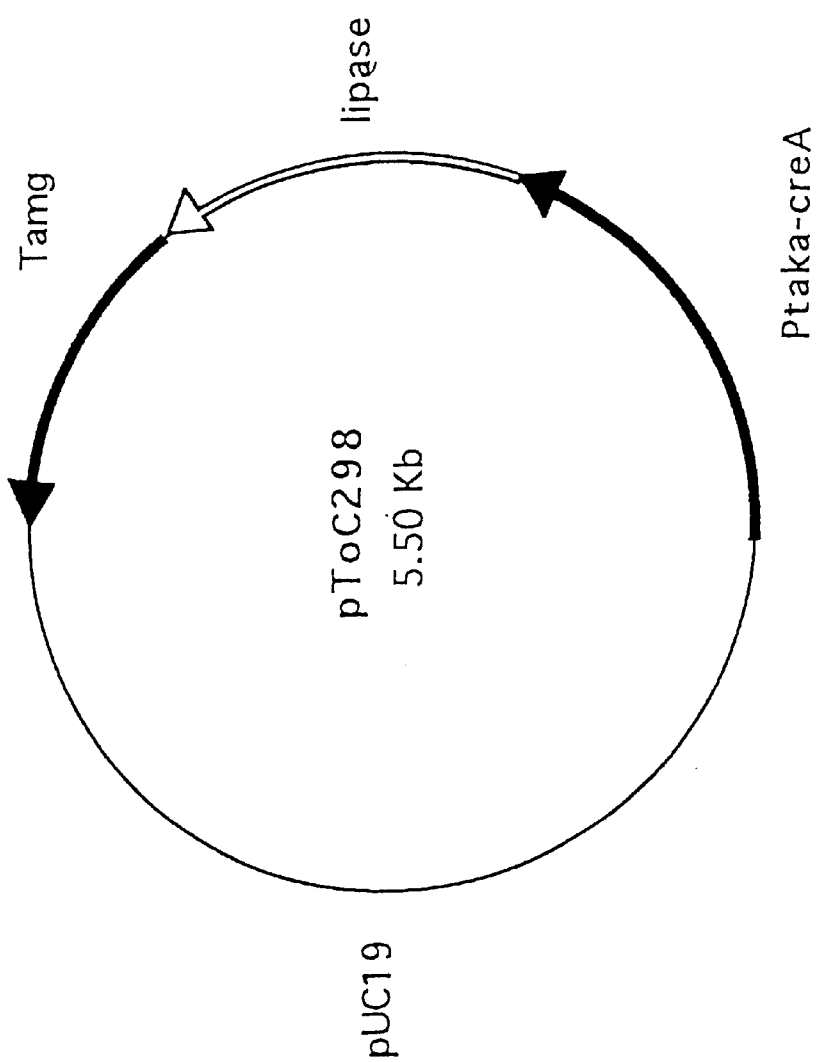
FIG. 5 shows the structure of the plasmid pToC298, the construction of which is described in Example 4.

A BamHI fragment of approximately 950bp containing the cDNA encoding a Humicola lanuginosa lipase was cloned into pToC297. (The cloning and expression of the H. lanuginosa lipase has been previously described in EP 305 216.) The resulting plasmid, pToC298, was transformed into A. oryzae IFO4177 by co-transformation with the A. nidulans amdS gene, and its structure is shown in FIG. 5, wherein Ptaka-creA represents the CreA binding site deficient TAKA-amalyase promoter. The transformants were reisolated twice through conidiospores and one such transformant, ToC1075, which produces lipase, was chosen for further evaluation. ToC1075 and a p960 transformant of IFO4177 (previously described in EP 305 216) containing the lipase fused to the wild type TAKA-promoter were grown at 30° C. in 10 ml YP containing 2% or 10% glucose. Samples were taken daily for analysis of lipase in the fermentation broth. The lipase content was measured by rocket immune electrophoresis using a polyclonal antibody raised against purified lipase. Spent fermentation broth from A. oryzae IFO4177 did not react with the antibody. The glucose content of the fermentation broth was likewise measured daily using Tes-tape from Lilly.

Figure 6:
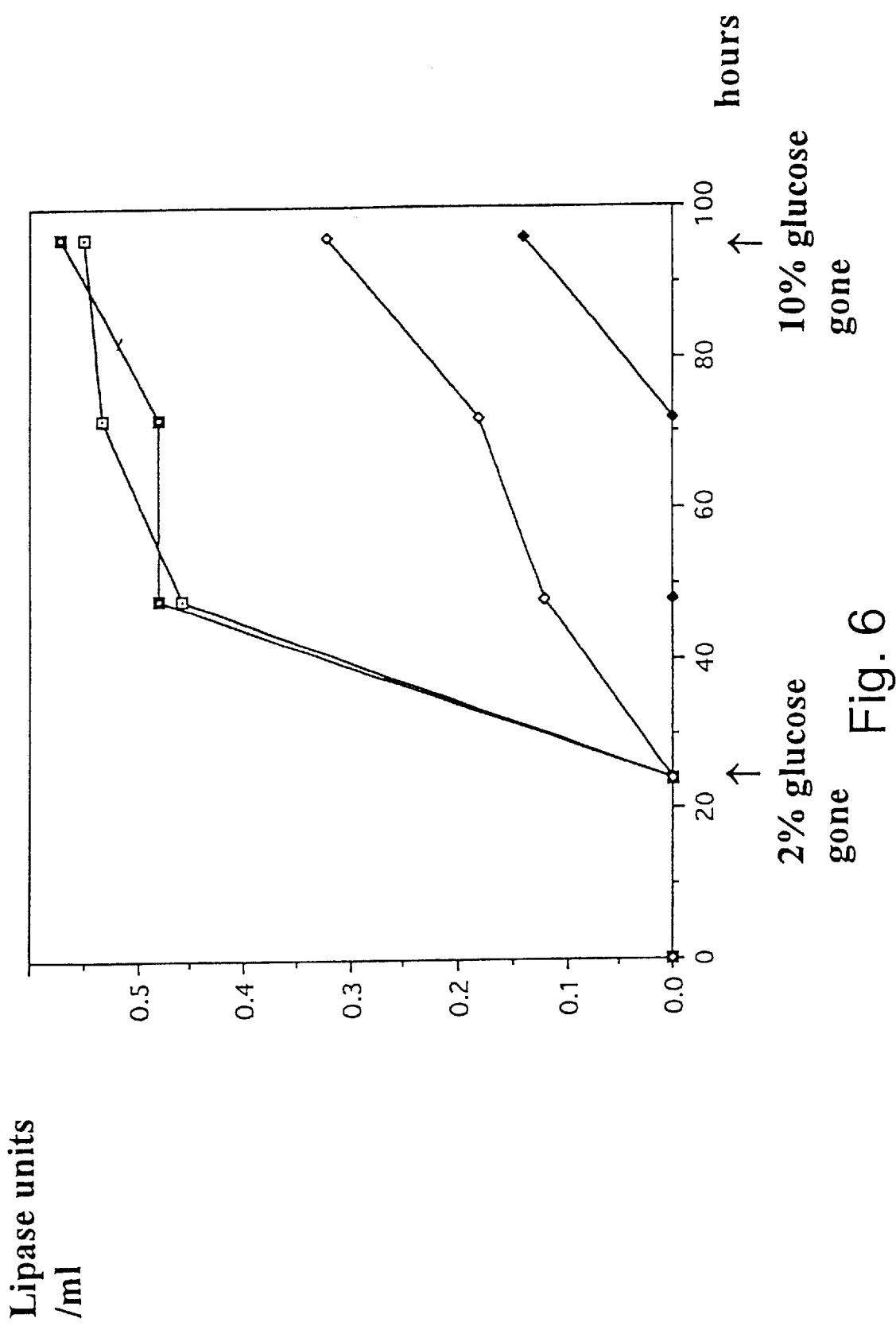
FIG. 6 shows the results of lipase production by a p960 transformant of *A. oryzae* IFO4177 cultured in YP media containing 2% glucose (-|-) or 10% glucose (-?-), in comparison to ToC1075 cultured in YP media containing 2% glucose (-⅋-) or 10% glucose (-◇-) and described in Example 4.

On day one, glucose was detected in all cultures, but on day two glucose could be detected only in cultures originally containing 10%. The results of lipase production, shown in FIG. 6, indicate that the wild type promoter is repressed until glucose is no longer present. Thus, when the glucose becomes exhausted, lipase begins to accumulate. FIG. 6 also shows that the modified promoter is not as tightly regulated, as low levels of lipase are produced in the presence of glucose in the 10% glucose fermentation. Thus, there is partial glucose derepression seen in ToC1075.

Relief of Carbon Catabolite Repression of Lipase in ToC1075 by pToC342

ToC1075 was transformed with pToC342 by co-transformation with the bar-containing plasmid, pMT1623. Strains containing multible copies of pToC342 and which retained the lipase expression cassette were identified by Southern blot analysis; one such strain was. ToC1075 and ToC1139 were grown at 30° C. in 10 ml YP containing either 2% or 10% glucose, and samples were assayed daily for lipase and glucose. The lipase was measured by cleavage of paranitrophenyl-butyrate. The glucose content was measured with Tes-tape from Lilly. The results, shown in FIG. 7, indicate that ToC1075, as before, provides partial relief of glucose repression while lipase production by ToC1139 is independent of the presence of glucose.

Example 5

Southern Analysis of A. niger for the amyR Gene

The syntheses of alpha-amylase and glucoamylase in A. niger, as in A. oryzae, are regulated by the carbon source. It is therefore likely that A. niger also contains an amyR gene. This hypothesis was tested by looking for cross-hybridization between the A. oryzae amyR gene and A. niger chromosomal DNA.

DNA was prepared from A. niger by conventional methods. The DNA was cut with BamHI, BgiII, EcoRI, HindIII, SalI, XmaI or XbaI, and the resulting DNA fragments were separated by electrophoresis on an agarose gel. The DNA was then blotted onto a nitrocellulase membrane and hybridized with a $^{32}$P-labelled probe containing part of the structural A. oryzae amyR gene. The probe was made by PCR on pToC320 and starts at bp. no. 1683 and ends at bp. no. 2615 as shown in SEQ ID NO: 1. The hybridization was conducted in 10×Denhardt's solution, 5×SSC, 10 mM EDTA, 1% SDS, 0.15 mg/ml polyA, 0.05 mg/ml yeast tRNA) at 50° C. overnight. After hybridization the membrane was washed under conditions of increasing stringency and the radioactivity on the membrane analysed by a PhosphoImager. FIG. 8 shows the result when the membrane had been washed in 2×SSC, 0.1%SDS at 58° C. Unique bands can be seen with several of the restriction enzymes. Thus, the A. niger amyR gene can be cloned on the basis of this cross-hybridization result.

REFERENCES CITED IN THE SPECIFICATION

Description

Dhawale and Lane (1993) *NAR* 21 5537–5546
Lachmund et al. (1993) *Current Microbiology* 26 47–51
Tada et al. (1991) *Mol. Gen. Genet* 229 301–306
Tada et al. (1991) *Agric. Biol. Chem.* 55 1939–1941
Tsuchiya et al. (1992) *Biosci. Biotech. Biochem.* 56 1849–1853,
Nagata et al. (1993) *Mol. Gen. Genet* 237 251–260
Ford et al., (1991), *Protein Expression and Purification* 2, 95–107
Cunningham and Wells, (1989) *Science* 244 1081–1085
Needleman, S. B. and Wunsch, C. D., (1970) *Journal of Molecular Biology* 48 443–453
Sambrook, J., et al., (1989), Molecular Cloning: A Laboratory Manual. Cold Spring Harbor Lab.; Cold Spring Harbor, N.Y.
WO 93/11249
WO 94/14953
Kelly and Kwon-Chung (1992) *J. Bacteriol.* 174 222–232
McKnight et al. (1985) *The EMBO J.* 4 2093–2099
EP 238 023
Kulmburg, P., et al. (1992) *Molecular and Cellular Biology* 12 1932–1939
Lutfiyya, L. L., and Johnston, M. (1996) *Molecular and Cellular Biology* 16 4790–4797

Examples

Feinberg, A. P. and Vogelstein, B. (1983) *Anal. Biochem.* 132:6–13
N. Axelsen et al. in: A Manual of Quantitative Immunoelectrophoresis, Blackwell Scientific Publications, 1973, Chapter 23
A. Johnstone and R. Thorpe, Immunochemistry in Practice, Blackwell Scientific Publications, 1982, pp. 27–31
O. Ouchterlony in: Handbook of Experimental Immunology (D. M. Weir, ed.), Blackwell Scientific Publications, 1967, pp. 655–706
D. Gems, I. L. Johnstone, and A. J. Clutterbuck, (1991) Gene 98 61–67
EP 531 372
B. Staubinger et al. (1992) *Fungal Genetics Newsletter* 39 82–83
M. E. Katz et al. (1990) *Mol. Gen. Genet.* 220 373–376
Christensen, T., et al., (1988) *Biotechnology* 6 1419–1422
Cove D. J., BBA (1966) 113 51–56
Reece, R. J., and Ptashne, M. (1993) *Science* 261 909–910
Wahleithner, J. A., et al. (1996) *Curr. Genet.* 29 395–403
Hata, Y., et al. (1992) *Curr. Genet.* 22 85–91
McKnight, G. L., et al, (1986, Cell 46 143–147)
DK1024/96
WO 95/35385
WO 91/17243
EP 305 216

I claim:

1. An isolated transcription factor capable of regulating transcription directed by a filamentous fungus alpha-amylase-promoter in a sequence-specific manner, which comprises an amino acid sequence which is at least 90% homologous with the amino acid sequence of SEQ ID NO: 3, when said homology is determined using GAP with a GAP creation penalty of 3.0 and a GAP extension penalty or a fragment thereof.

2. The transcription factor of claim 1, which comprises the amino acid sequence of SEQ ID NO: 3 or a fragment thereof.

3. The transcription factor of claim 2, which comprises the amino acid sequence of SEQ ID NO: 3.

4. An isolated transcription factor which exhibits activity in regulating the expression of an alpha-amylase promoter in a filamentous fungus, which is encoded by:

(a) the transcription factor-encoding part of the DNA sequence cloned into plasmid pToC320 present in *E. coli*, DSM 10666, or (b) a DNA sequence which is at least 70% homologous with the DNA sequence defined in (a), when said homology is determined using GAP with a GAP creation penalty of 5.0 and a GAP extension penalty of 0.3

5. The transcription factor of claim 4, wherein the DNA sequence is obtained from a filamentous fungus.

6. The transcription factor of claim 5, wherein the filamentous fungus is selected from the group consisting of Ascomycetes, Basidiomycetes Phycomycetes, Zygomycetes, and fungi imperfecti.-

7. The transcription factor of claim 5, wherein the filamentous fungus is selected from the group consisting of Aspergillus, Fusarium, Humicola, Penicillium, and Trichoderma.

8. The transcription factor of claim 7, wherein the filamentous fungus is Fusarium.

9. The transcription factor of claim 7, wherein the filamentous fungus is *A. awamori, A. niger,* or *A. oryzae.*

10. The transcription factor of claim 9, wherein the filamentous fungus is *Aspergillus oryzae.*

11. The transcription factor of claim 10, wherein the filamentous fungus is *A. oryzae,* IFO4177.

12. The transcription factor of claim 4, wherein the DNA sequence is obtained from a yeast strain.

13. The transcription factor of claim 4, wherein the DNA sequence is obtained from *Eschericia coli,* DSM 10666.

* * * * *

SEQUENCE LISTING

<160> NUMBER OF SEQ ID NOS: 14

<210> SEQ ID NO 1
<211> LENGTH: 3980
<212> TYPE: DNA
<213> ORGANISM: Aspergillus oryzae

<400> SEQUENCE: 1

-continued

```
tctagaccgg ccatgtcgtg gtccgccaag ttgattccgg accgtgttgt agttgcttct      60
tttaagaaac ggcacccctc tgccgtctcc gaaccggaat tgtagctaga tgtatatgtc     120
ttgacgaacc aggtgtccac gggcaaatcc ctcacaattg atggcccgtc ccgttcccat     180
cgatttgtgc tacctgccgt gcaaggcaaa acatccccgt caaacgtccg aggggcattg     240
cctgcaatct ctcgaccatg agaggggaag caagtcacgc tagttgcaag ggtataggtc     300
ctacgcagca atgaggtggc ttcacccgta cggagtgggg acagcatgat caagcctttt     360
gggaacgtga cgaaagagta ccggttaagc cgacgatggg agatgaatct ctgccgagca     420
aaggacgaga ccggaaaaga gtgtgttgat tcttgggagc agttacagta cttccgtgtc     480
cggaaattgg aaacgttcct gaccaatgct ggcgatcatc tgatatccct acgctgattg     540
gtccatcccc cgataaatgc ccgacacgac gcttgagccc tgaaaggta gtatttctcg      600 agagatccat tcaccagagt caatactggc aaatacatcg ttccccacct catattccaa     660
ggtgcctaaa cccctccggt gtgccggtga gggttttcca cgccatctct agtggtgcca     720
tgacgggagc atccgatggc ttccagtatt gggtggttgg gatggacaac aagctccaaa     780 taagggaat ttgcctttgg tccaggaatg aagtccccgt ggggaccagc ggctcagccc      840
aggctaagag tggaatatcg tcatagacct tcggctcatg ggaggttcgg aggtgttacg     900
atcctcttca atgccattca ttctctgttt tgacctcggc ttcccgagag tggtgcctcc     960
cttacatccc cacatgctgg atgcaagcct gtggtacgct gtttctttca gaagtagcag    1020
gctaggttca cgatgagctg cctttcaaac ctggaataac cattacgtga gactgttcta    1080
cttcttgaat tgatccctga ctagagtctg ctctaatatg ctgtgtggca cggccggtcc    1140
cctcggggtt gctaaggctg atttatgcac tccgtacagt ataacccagg gtggctatag    1200
attccctgca tcttccacgc tccctcacaa cctgattcca ccattcttaa gcggccgtta    1260
gcctcgatgg ggtataatgg agttaactat aaacacgact ctacaacgaa tcccgatgtg    1320
agtttggaac gagttgttac cgatgggtcc tcccatttgt taggagtgac gctaggggac    1380
ctttagggca cagactaaac caagacaaag atggagtaga ctccaggtag attaattcca    1440
atcttcttgc caaagtaacg cggggttttt tgcacctgca gcctcttttt tttcttttt     1500 cttttttttc ttttttttatt gttccccaga tttcttttct ttttcttcaa tcctgacgtt    1560
ctcaaccgtg atggcgacac agcccgcttc gctatccctc gcttttacgt cggccattct    1620
tctagttgct ctcgcgggat gccatgattt ctaaaggctc cacatcggcg agatagtatc    1680
ctatccgagc atgtctcatt ctccaaccga cattccctca acatccgaaa aggaaatgga    1740
gtcaacccca gaaaagccgc ctaaacaggc ctgcgacaat gccgtcgac gcaaaatcaa     1800 gtgttctaga gagcttccat gcgacaagtg ccagcgtctt cttctctcct gttcctacag    1860
cgacgtgctc cgtcgcaagg gccccaagtt ccgcacgctc taccctctcg ctcccatcca    1920
tccactcgcc tcacgaccac gtcctctcac caaggaatgg ctgcccccaa acccagggggc   1980 ttgccatttg gcgtccccga cgtctccgcc gtccaccgta gcggacgccc agtatctaca    2040
tccagacttc tcggagtcgt tcactcgact accacccccca gatctcgtct cctctcccga   2100
ctcgacaaac tcgctattcg actcgtccac tatcggcgca ctccccgcgc acgccgtct    2160 gtcgacgcca aacttctag cccatgtcaa tgtcttcctc aagtacctgt tcccgatcat     2220
gcccgtcgtg agacaggacc agctgcagca ggactgccac cagccggagc gcttgtctcc    2280
ccaacgctac gctttcattg ccgctctatg cgcggccacg cacatccaac tgaagctgga    2340
cggtgcagca ccgggtcccg aggcggcttc cgcgcgagcc agcctcgacg gacatcctat    2400
```

-continued

```
gttgtcggga gaagaactcc tggctgaagc cgtgcgcgca agaaaggaat acaacgtggt    2460
cgacgaaatt aacatggaaa acctcctaac ctccttcttt ctcttcgccg cctacgaaaa    2520
cctagacaga caggatcagg cctggttcta cctatgtcag accacgtcca tggtcttcac    2580
actaggccta caacgggaat ccacatactc gaaactaagc gtcgaggaag cagaagagaa    2640
aaggagagta ttctggctct tattcgtcac agaaaggtaa gaaaagaaaa aactctactt    2700
tcccaatcac caccacgtac caaaaataac acgaaaaacc agaggctacg cattacaaca    2760
agcaaaacca gtcatgctcc gcaactccat ccacaaacca caggtcctgt gctcagacga    2820
cccaatccta gcctacgggt tcatcaacct catcaacgtc ttcgaaaagc tcagcccaaa    2880
tctctacgac tgggtctccg ccggcggcag cagcgcagac ggcgaccccc cgcctacttc    2940
ttctatccaa tccagtctcg ccaagcaaat ctccctcgag ggcgtctccg agatccagaa    3000
agtagacatc ctcatcactc agcaatggct acaaaccatg atgtggaaac tctccatgac    3060
ccacgtcaca cagcccggct ctcgcgatga cgccgttctc cccttccacc tgcccgtgct    3120
agtcggcaag gccgtcatgg gcgtcatcgc cgcggcatcc caaggtgctg ttgacgctca    3180
tggtatcgga atggtaagaa agcgacctta cctcatcaca ccctccctca tcagtcactc    3240
cccatcatct atacccgcaa tctaacaaaa accgcaggaa caaaaactct acgacctcgg    3300
cacctccgta gccgacgtct cccgctccct aagcacaaaa gccgccacc acctcgccga    3360
atcgaccatc gaccccgag aactcctctg gggcattctc acaaccctat cccgaatccg    3420
cggttcccaa tcatacctct tcccagcgct cgtcgagcaa agtcgaggca tcatcagttt    3480
cgactgttcg ctttccatca gtgactttct gccttcgttt ggtgggccgc cggctattat    3540
gtggcggacg ggtgaatctg ggtttgattt attggggatc gcggatgatt tgcaagagag    3600
ggagaatgag ggtggggagg ggattgtggt ggctggggag gagatttcgt tttgagggg    3660
ctctttcctt tttcctttgt ggtgtgttgt gttgggtggt tctgggggg cggggtgta    3720
tatacgcttg acgatgtgca ttgggattgg ggttcctact ggtatataat atggattgtt    3780
ttgtatatag tccgctggag acggtgcaat gatgtgggga tcaatcactt cttaggactc    3840
ggagcacagg gtgtcggttc tcgggttatt ctgagtatga gattatatag aatcagttaa    3900
tgatcattat tgtacatacc ttaaagaaag atatgcttgg caccccgata tgacaataga    3960
aaactggtct tcattctaga                                                3980
```

<210> SEQ ID NO 2
<211> LENGTH: 3980
<212> TYPE: DNA
<213> ORGANISM: Aspergillus oryzae

<400> SEQUENCE: 2

```
tctagaccgg ccatgtcgtg gtccgccaag ttgattccgg accgtgttgt agttgcttct      60
tttaagaaac ggcacccctc tgccgtctcc gaaccggaat tgtagctaga tgtatatgtc     120
ttgacgaacc aggtgtccac gggcaaatcc ctcacaattg atggcccgtc ccgttcccat     180
cgatttgtgc tacctgccgt gcaaggcaaa acatccccgt caaacgtccg aggggcattg     240
cctgcaatct ctcgaccatg agagggaag caagtcacgc tagttgcaag ggtataggtc     300
ctacgcagca atgaggtggc ttcacccgta cggagtgggg acagcatgat caagcctttt     360
gggaacgtga cgaaagagta ccggttaagc cgacgatggg agatgaatct ctgccgagca     420
aaggacgaga ccggaaaaga gtgtgttgat tcttgggagc agttacagta cttccgtgtc     480
```

-continued

```
cggaaattgg aaacgttcct gaccaatgct ggcgatcatc tgatatccct acgctgattg      540
gtccatcccc cgataaatgc ccgacacgac gcttgagccc tgaaaaggta gtatttctcg      600
agagatccat tcaccagagt caatactggc aaatacatcg ttccccacct catattccaa      660
ggtgcctaaa ccctccggt gtgccggtga gggttttcca cgccatctct agtggtgcca       720
tgacgggagc atccgatggc ttccagtatt ggtggttgg gatggacaac aagctccaaa       780 taagggaat ttgcctttgg tccaggaatg aagtcccgt ggggaccagc ggctcagccc        840
aggctaagag tggaatatcg tcatagacct tcggctcatg ggaggttcgg aggtgttacg      900
atcctcttca atgccattca ttctctgttt tgacctcggc ttcccgagag tggtgcctcc      960
cttacatccc cacatgctgg atgcaagcct gtggtacgct gtttctttca gaagtagcag     1020
gctaggttca cgatgagctg cctttcaaac ctggaataac cattacgtga gactgttcta    1080
cttcttgaat tgatccctga ctagagtctg ctctaatatg ctgtgtggca cggccggtcc    1140
cctcggggtt gctaaggctg atttatgcac tccgtacagt ataacccagg gtggctatag   1200
attccctgca tcttccacgc tccctcacaa cctgattcca ccattcttaa gcggccgtta   1260
gcctcgatgg ggtataatgg agttaactat aaacacgact ctacaacgaa tcccgatgtg   1320
agtttggaac gagttgttac cgatgggtcc tcccatttgt taggagtgac gctaggggac   1380
ctttagggca cagactaaac caagacaaag atggagtaga ctccaggtag attaattcca   1440
atcttcttgc caaagtaacg cggggttttt tgcacctgca gcctcttttt tttcttttt    1500 cttttttttc tttttttatt gttccccaga tttcttttct ttttcttcaa tcctgacgtt   1560
ctcaaccgtg atggcgacac agcccgcttc gctatccctc gcttttacgt cggccattct   1620
tctagttgct ctcgcgggat gccatgattt ctaaaggctc cacatcggcg agatagtatc   1680
ctatccgagc atgtctcatt ctccaaccga cattccctca acatccgaaa aggaaatgga   1740 gtcaaccca gaaaagccgc ctaaacaggc ctgcgacaat gccgtcgac gcaaaatcaa     1800 gtgttctaga gagcttccat gcgacaagtg ccagcgtctt cttctctcct gttcctacag   1860
cgacgtgctc cgtcgcaagg gccccaagtt ccgcacgctc taccctctcg ctcccatcca   1920
tccactcgcc tcacgaccac gtcctctcac caaggaatgg ctgcccccaa acccaggggc   1980
ttgccatttg gcgtccccga cgtctccgcc gtccaccgta gcggacgccc agtatctaca   2040
tccagacttc tcggagtcgt tcactcgact accaccccca gatctcgtct cctctcccga   2100
ctcgacaaac tcgctattcg actcgtccac tatcggcgca ctccccgcgc cacgccgtct   2160
gtcgacgcca aaccttctag cccatgtcaa tgtcttcctc aagtacctgt tcccgatcat   2220
gcccgtcgtg agacaggacc agctgcagca ggactgccac cagccggagc gcttgtctcc   2280
ccaacgctac gctttcattg ccgctctatg cgcggccacg cacatccaac tgaagctgga   2340
cggtgcagca ccgggtcccg aggcggcttc cgcgcgagcc agcctcgacg gacatcctat   2400
gttgtcggga gaagaactcc tggctgaagc cgtgcgcgca agaaaggaat acaacgtggt   2460
cgacgaaatt aacatggaaa acctcctaac ctccttcttt ctcttcgccg cctacgaaa    2520 cctagacaga caggatcagg cctggttcta cctatgtcag accacgtcca tggtcttcac   2580
actaggccta caacgggaat ccacatactc gaaactaagc gtcgaggaag cagaagagaa   2640
aaggagagta ttctggctct tattcgtcac agaaaggtaa gaaaagaaaa aactctactt   2700
tcccaatcac caccacgtac caaaaataac acgaaaaacc agaggctacg cattacaaca   2760
agcaaaacca gtcatgctcc gcaactccat ccacaaacca caggtcctgt gctcagacga   2820
cccaatccta gcctacgggt tcatcaacct catcaacgtc ttcgaaaagc tcagcccaaa   2880
```

-continued

```
tctctacgac tgggtctccg ccggcggcag cagcgcagac ggcgaccccc cgcctacttc    2940
ttctatccaa tccagtctcg ccaagcaaat ctccctcgag ggcgtctccg agatccagaa    3000
agtagacatc ctcatcactc agcaatggct acaaaccatg atgtggaaac tctccatgac    3060
ccacgtcaca cagcccggct ctcgcgatga cgccgttctc cccttccacc tgcccgtgct    3120
agtcggcaag gccgtcatgg gcgtcatcgc cgcggcatcc caaggtgctg ttgacgctca    3180
tggtatcgga atggtaagaa agcgacctta cctcatcaca ccctccctca tcagtcactc    3240
cccatcatct ataccgcaa tctaacaaaa accgcaggaa caaaaactct acgacctcgg    3300
cacctccgta gccgacgtct cccgctccct aagcacaaaa gccgcccacc acctcgccga    3360
atcgaccatc gaccccgag aactcctctg gggcattctc acaaccctat cccgaatccg    3420
cggttcccaa tcatacctct tcccagcgct cgtcgagcaa agtcgaggca tcatcagttt    3480
cgactgttcg ctttccatca gtgactttct gccttcgttt ggtgggccgc cggctattat    3540
gtggcggacg ggtgaatctg ggtttgattt attggggatc gcggatgatt tgcaagagag    3600
ggagaatgag ggtggggagg ggattgtggt ggctggggag gagatttcgt tttgaggggg    3660
ctcttttctt tttcctttgt ggtgtgttgt gttgggtggt tctgggggg cggggtgta    3720
tatacgcttg acgatgtgca ttgggattgg ggttcctact ggtatataat atggattgtt    3780
ttgtatatag tccgctggag acggtgcaat gatgtgggga tcaatcactt cttaggactc    3840
ggagcacagg gtgtcggttc tcgggttatt ctgagtatga gattatatag aatcagttaa    3900
tgatcattat tgtacatacc ttaaagaaag atatgcttgg caccccgata tgacaataga    3960
aaactggtct tcattctaga                                                3980
```

<210> SEQ ID NO 3
<211> LENGTH: 604
<212> TYPE: PRT
<213> ORGANISM: Aspergillus oryzae

<400> SEQUENCE: 3

```
Met Ser His Ser Pro Thr Asp Ile Pro Ser Thr Ser Glu Lys Glu Met
 1               5                  10                  15

Glu Ser Thr Pro Glu Lys Pro Pro Lys Gln Ala Cys Asp Asn Cys Arg
            20                  25                  30

Arg Arg Lys Ile Lys Cys Ser Arg Glu Leu Pro Cys Asp Lys Cys Gln
        35                  40                  45

Arg Leu Leu Leu Ser Cys Ser Tyr Ser Asp Val Leu Arg Arg Lys Gly
    50                  55                  60

Pro Lys Phe Arg Thr Leu Tyr Pro Leu Ala Pro Ile His Pro Leu Ala
65                  70                  75                  80

Ser Arg Pro Arg Pro Leu Thr Lys Glu Trp Leu Pro Asn Pro Gly
                85                  90                  95

Ala Cys His Leu Ala Ser Pro Thr Ser Pro Pro Ser Thr Val Ala Asp
            100                 105                 110

Ala Gln Tyr Leu His Pro Asp Phe Ser Glu Ser Phe Thr Arg Leu Pro
        115                 120                 125

Pro Pro Asp Leu Val Ser Ser Pro Asp Ser Thr Asn Ser Leu Phe Asp
    130                 135                 140

Ser Ser Thr Ile Gly Ala Leu Pro Ala Pro Arg Arg Leu Ser Thr Pro
145                 150                 155                 160

Asn Leu Leu Ala His Val Asn Val Phe Leu Lys Tyr Leu Phe Pro Ile
                165                 170                 175
```

```
Met Pro Val Val Arg Gln Asp Gln Leu Gln Gln Asp Cys His Gln Pro
            180                 185                 190

Glu Arg Leu Ser Pro Gln Arg Tyr Ala Phe Ile Ala Ala Leu Cys Ala
            195                 200                 205

Ala Thr His Ile Gln Leu Lys Leu Asp Gly Ala Ala Pro Gly Pro Glu
            210                 215                 220

Ala Ala Ser Ala Arg Ala Ser Leu Asp Gly His Pro Met Leu Ser Gly
225                 230                 235                 240

Glu Glu Leu Leu Ala Glu Ala Val Arg Ala Arg Lys Glu Tyr Asn Val
                245                 250                 255

Val Asp Glu Ile Asn Met Glu Asn Leu Leu Thr Ser Phe Phe Leu Phe
            260                 265                 270

Ala Ala Tyr Gly Asn Leu Asp Arg Gln Asp Gln Ala Trp Phe Tyr Leu
            275                 280                 285

Cys Gln Thr Thr Ser Met Val Phe Thr Leu Gly Leu Gln Arg Glu Ser
            290                 295                 300

Thr Tyr Ser Lys Leu Ser Val Glu Glu Ala Glu Glu Lys Arg Arg Val
305                 310                 315                 320

Phe Trp Leu Leu Phe Val Thr Glu Arg Gly Tyr Ala Leu Gln Gln Ala
                325                 330                 335

Lys Pro Val Met Leu Arg Asn Ser Ile His Lys Pro Gln Val Leu Cys
            340                 345                 350

Ser Asp Asp Pro Ile Leu Ala Tyr Gly Phe Ile Asn Leu Ile Asn Val
            355                 360                 365

Phe Glu Lys Leu Ser Pro Asn Leu Tyr Asp Trp Val Ser Ala Gly Gly
            370                 375                 380

Ser Ser Ala Asp Gly Asp Pro Pro Thr Ser Ser Ile Gln Ser Ser
385                 390                 395                 400

Leu Ala Lys Gln Ile Ser Leu Glu Gly Val Ser Glu Ile Gln Lys Val
                405                 410                 415

Asp Ile Leu Ile Thr Gln Gln Trp Leu Gln Thr Met Met Trp Lys Leu
            420                 425                 430

Ser Met Thr His Val Thr Gln Pro Gly Ser Arg Asp Asp Ala Val Leu
            435                 440                 445

Pro Phe His Leu Pro Val Leu Val Gly Lys Ala Val Met Gly Val Ile
            450                 455                 460

Ala Ala Ala Ser Gln Gly Ala Val Asp Ala His Gly Ile Gly Met Glu
465                 470                 475                 480

Gln Lys Leu Tyr Asp Leu Gly Thr Ser Val Ala Asp Val Ser Arg Ser
                485                 490                 495

Leu Ser Thr Lys Ala Ala His His Leu Ala Glu Ser Thr Ile Asp Pro
            500                 505                 510

Arg Glu Leu Leu Trp Gly Ile Leu Thr Thr Leu Ser Arg Ile Arg Gly
            515                 520                 525

Ser Gln Ser Tyr Leu Phe Pro Ala Leu Val Glu Gln Ser Arg Gly Ile
            530                 535                 540

Ile Ser Phe Asp Cys Ser Leu Ser Ile Ser Asp Phe Leu Pro Ser Phe
545                 550                 555                 560

Gly Gly Pro Pro Ala Ile Met Trp Arg Thr Gly Glu Ser Gly Phe Asp
                565                 570                 575

Leu Leu Gly Ile Ala Asp Asp Leu Gln Glu Arg Glu Asn Glu Gly Gly
            580                 585                 590
```

-continued

Glu Gly Ile Val Val Ala Gly Glu Glu Ile Ser Phe
            595                 600

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
cttgcatgcc gccaggaccg agcaag                                    26

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
cttggatcct ctgtgttagc ttatag                                    26

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
ccccaagctt cgccgtctgc gctgctgccg                                30

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
cggaattcat caacctcatc aacgtcttc                                 29

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
cggaattcat cggcgagata gtatcctat                                 29

<210> SEQ ID NO 9
<211> LENGTH: 41
<212> TYPE: DNA
<213> ORGANISM: Artificial Sequence
<220> FEATURE:
<223> OTHER INFORMATION: Primer

<400> SEQUENCE: 9
ttttgtaagc tttttttttt tttttttttt tttttttttt t                   41

<210> SEQ ID NO 10
<211> LENGTH: 20
<212> TYPE: DNA

```
<213> ORGANISM: Artificial Sequence
<220> FEATURE:
<223> OTHER INFORMATION: Primer

<400> SEQUENCE: 10
gtttcgagta tgtggattcc                                               20

<210> SEQ ID NO 11
<211> LENGTH: 31
<212> TYPE: DNA
<213> ORGANISM: Artificial Sequence
<220> FEATURE:
<223> OTHER INFORMATION: Primers

<400> SEQUENCE: 11
cggaattcgg atccgagcat gtctcattct c                                  31

<210> SEQ ID NO 12
<211> LENGTH: 11
<212> TYPE: DNA
<213> ORGANISM: Artificial Sequence
<220> FEATURE:
<223> OTHER INFORMATION: Primers

<400> SEQUENCE: 12
ccccggtatt g                                                        11

<210> SEQ ID NO 13
<211> LENGTH: 11
<212> TYPE: DNA
<213> ORGANISM: Artificial Sequence
<220> FEATURE:
<223> OTHER INFORMATION: Primer

<400> SEQUENCE: 13
ccccggagtc a                                                        11

<210> SEQ ID NO 14
<211> LENGTH: 11
<212> TYPE: DNA
<213> ORGANISM: Artificial Sequence
<220> FEATURE:
<223> OTHER INFORMATION: Primer

<400> SEQUENCE: 14
atatggcggg t                                                        11
```